US012220313B2

(12) United States Patent
Hariton et al.

(10) Patent No.: US 12,220,313 B2
(45) Date of Patent: *Feb. 11, 2025

(54) SYSTEMS AND METHODS FOR IMPLANTING A PROSTHETIC VALVE WITHIN A NATIVE HEART VALVE

(71) Applicant: CARDIOVALVE LTD., Or Yehuda (IL)

(72) Inventors: Ilia Hariton, Zichron Yaackov (IL); Meni Iamberger, Kfar Saba (IL); Aviram Baum, Tel Aviv (IL); Boaz Harari, Ganey Tikva (IL)

(73) Assignee: CARDIOVALVE LTD., Or Yehuda (IL)

( * ) Notice: Subject to any disclaimer, the term of this patent is extended or adjusted under 35 U.S.C. 154(b) by 0 days.

This patent is subject to a terminal disclaimer.

(21) Appl. No.: 18/109,937

(22) Filed: Feb. 15, 2023

(65) Prior Publication Data

US 2023/0190461 A1    Jun. 22, 2023

Related U.S. Application Data

(63) Continuation of application No. 16/135,466, filed on Sep. 19, 2018.

(Continued)

(51) Int. Cl.
A61F 2/24    (2006.01)

(52) U.S. Cl.
CPC .......... *A61F 2/2427* (2013.01); *A61F 2/243* (2013.01); *A61F 2/2436* (2013.01);
(Continued)

(58) Field of Classification Search
CPC ........ A61F 2/243; A61F 2/246; A61F 2/2466; A61F 2220/0008; A61F 2/2436
See application file for complete search history.

(56) References Cited

U.S. PATENT DOCUMENTS

| | | | |
|---|---|---|---|
| 10,322,020 B2 | 6/2019 | Lam et al. | |
| 10,463,488 B2 * | 11/2019 | Hariton | ................. A61F 2/2418 623/2.14 |

(Continued)

FOREIGN PATENT DOCUMENTS

| | | |
|---|---|---|
| WO | 2009/091509 A1 | 7/2009 |
| WO | 2010/045297 A2 | 4/2010 |
| WO | 2016/016899 A1 | 2/2016 |

*Primary Examiner* — Brian E Pellegrino
(74) *Attorney, Agent, or Firm* — Sughrue Mion, PLLC

(57) ABSTRACT

An expandable prosthetic valve is implantable within a native mitral valve by terminal ends of ventricular anchors of the prosthetic valve moving outwardly from a constrained delivery position of the ventricular anchors, while the ventricular anchors are positioned within the atrium. Then, a portion of the expandable prosthetic valve containing the ventricular anchors is advanced through the native mitral valve into the ventricle. Terminal ends of atrial anchors of the prosthetic valve move outwardly relative to a portion of an annular valve body of the prosthetic valve while the atrial anchors are at least partially positioned within the atrium. Next, the annular valve body is radially expanded while the ventricular anchors are in the ventricle and the atrial anchors are in the atrium, thereby anchoring native heart valve tissue between the atrial anchors and ventricular anchors. Other embodiments are also described.

9 Claims, 21 Drawing Sheets

Related U.S. Application Data

(60) Provisional application No. 62/560,384, filed on Sep. 19, 2017.

(52) U.S. Cl.
CPC .......... *A61F 2/2445* (2013.01); *A61F 2/2454* (2013.01); *A61F 2/2463* (2013.01); *A61F 2/2409* (2013.01); *A61F 2/2418* (2013.01); *A61F 2/246* (2013.01); *A61F 2/2466* (2013.01); *A61F 2210/0014* (2013.01); *A61F 2220/0008* (2013.01); *A61F 2250/007* (2013.01)

(56) References Cited

U.S. PATENT DOCUMENTS

| | | |
|---|---|---|
| 10,842,627 B2 | 11/2020 | Delgado et al. |
| 2008/0071361 A1 | 3/2008 | Tuval et al. |
| 2008/0147182 A1 | 6/2008 | Righini et al. |
| 2009/0105794 A1 | 4/2009 | Ziarno et al. |
| 2013/0274870 A1 | 10/2013 | Lombardi et al. |
| 2014/0067050 A1 | 3/2014 | Costello et al. |
| 2014/0249622 A1* | 9/2014 | Carmi ................ A61F 2/2418 623/2.11 |
| 2015/0351903 A1 | 12/2015 | Morriss et al. |
| 2015/0351904 A1* | 12/2015 | Cooper ................ A61F 2/2418 623/2.1 |
| 2016/0310268 A1 | 10/2016 | Oba et al. |
| 2019/0008640 A1* | 1/2019 | Cooper ................ A61F 2/2436 623/2.17 |

\* cited by examiner

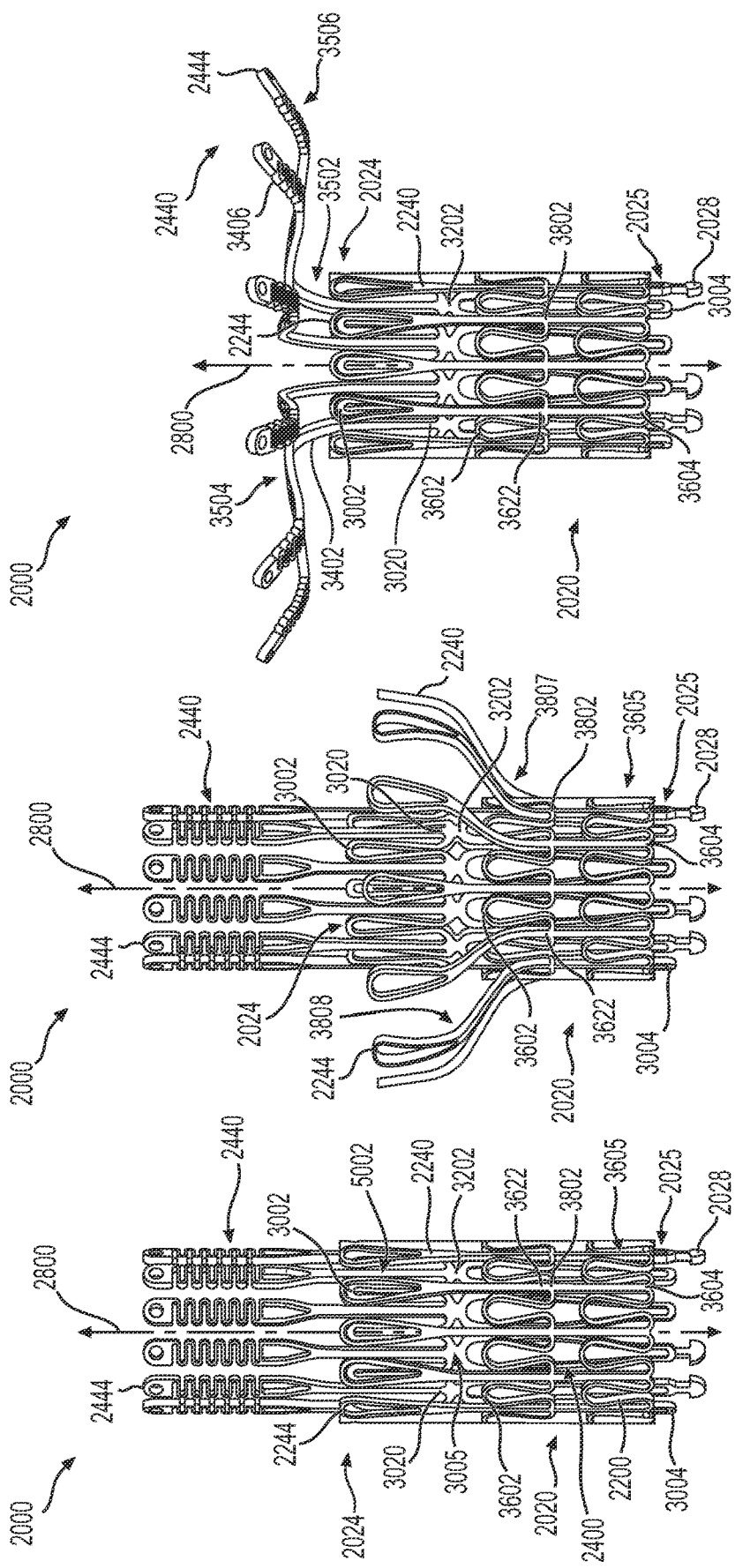

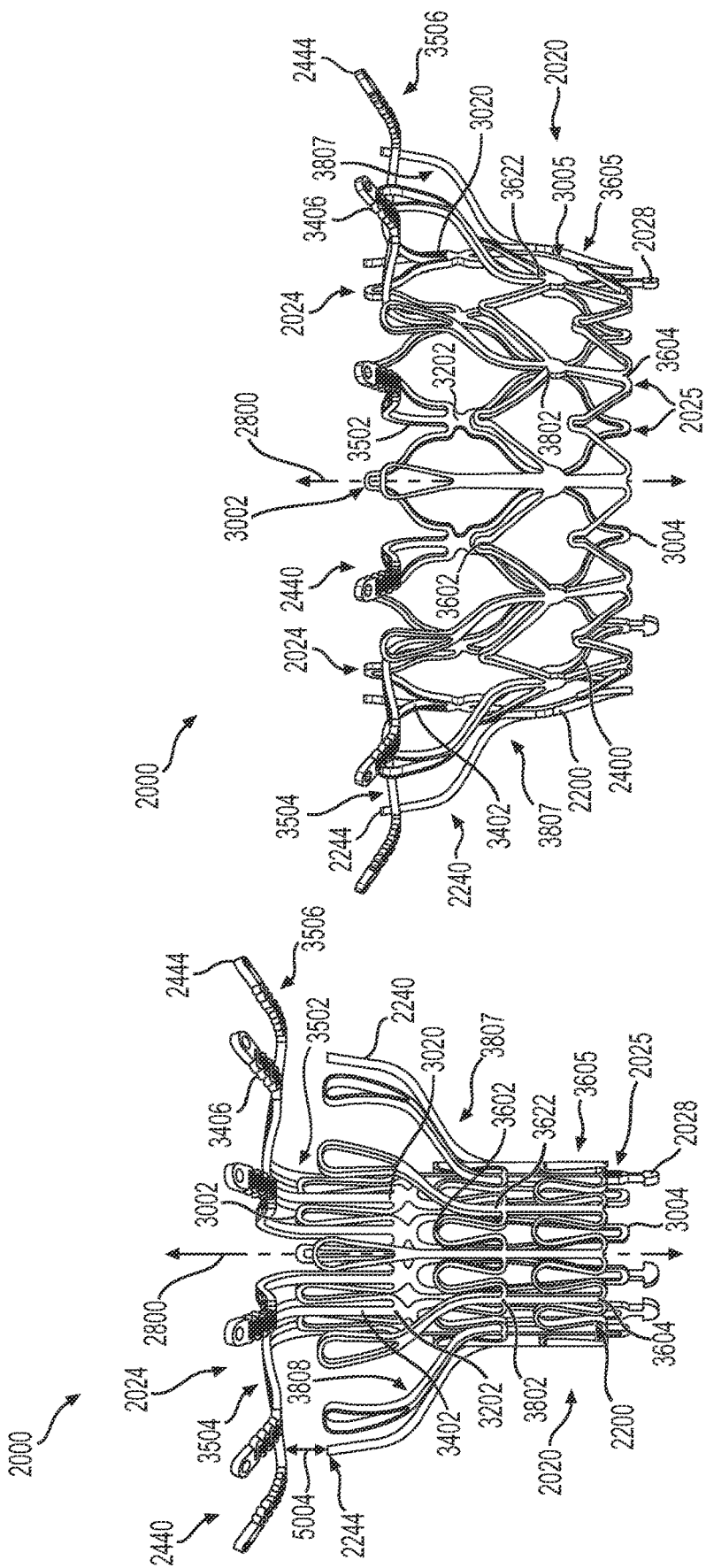

SYSTEMS AND METHODS FOR IMPLANTING A PROSTHETIC VALVE WITHIN A NATIVE HEART VALVE

CROSS-REFERENCE TO RELATED APPLICATION

This application is a continuation application of U.S. patent application Ser. No. 16/135,466, filed Sep. 19, 2018, which published as US 2019/0083242 to Hariton et al., and which claims priority from U.S. Provisional Patent Application No. 62/560,384, filed Sep. 19, 2017. These applications are hereby incorporated by reference in their entirety.

TECHNICAL FIELD

This disclosure relates generally to systems and methods for implanting prosthetic valves within a native heart valve. More specifically, this disclosure relates to methods for implanting an expandable prosthetic valve within a native mitral valve that include releasing a plurality of ventricular anchors and a plurality of atrial anchors within an atrium of the heart.

BACKGROUND

The native heart valves (the tricuspid valve, pulmonary valve, mitral valve, and aortic valve) play an important role in regulating flow of blood through the cardiovascular system. However, the native heart valves may become damaged or impaired due to, for example, cardiovascular diseases, infections, or congenital malformations, thus limiting the ability of the native heart valves to regulate blood flow. This deficiency may result in reduced cardiovascular function or even death.

To treat these conditions, prosthetic heart valves may be implanted at or near the site of a damaged or impaired native valve. A prosthetic heart valve may assist or replace the functionality of an impaired native valve, leading to better regulation of blood flow and improved cardiovascular function. However, many existing prosthetic heart valves require implantation via an open heart procedure, which is highly-invasive and may cause life-threatening complications. Other prosthetic valves may be collapsed within a prosthetic valve delivery system and advanced into the heart, at which point the prosthetic valve may be removed from the delivery system and expanded at the native valve site. However, many of these prosthetic valves are large in size and therefore difficult to deliver into the heart without causing damage to healthy tissue along the implantation route. In addition, once these prosthetic valves are situated within the heart, they may be difficult to securely implant at the native valve site due to their complex structure and the limited maneuverability of existing prosthetic valve delivery systems within the heart. Moreover, many prosthetic valves are so large that they may protrude several centimeters into surrounding heart chambers once they are implanted, impairing cardiac filling and causing injury to the anatomy within the heart.

Thus, there remains a need for prosthetic heart valves that are smaller in size but that are still configured to assist or replace the functionality of a diseased or damaged native heart valve. In addition, there remains a need for prosthetic heart valves that are more easily maneuvered into the heart and securely implanted at the site of a native heart valve. Moreover, there remains a need for improved prosthetic heart valve delivery systems that are configured to securely implant a prosthetic heart valve at an implantation site. The present disclosure provides prosthetic heart valves with a reduced axial length such that the prosthetic heart valves may be more easily delivered into the heart and may exhibit less protrusion into the chambers of the heart. The present disclosure also provides improved prosthetic heart valve delivery systems and methods of implanting prosthetic heart valves, such that prosthetic heart valves may be securely anchored at the implantation site.

SUMMARY

The present disclosure discloses prosthetic valves for implantation within a native mitral valve and methods for implanting prosthetic valves within a native mitral valve. Particular examples of the disclosure may pertain to a method of implanting a prosthetic valve within a native mitral valve including releasing a plurality of ventricular anchors and a plurality of atrial anchors within an atrium.

According to an exemplary embodiment of the present disclosure, a method of implanting an expandable prosthetic valve within a native mitral valve between a heart atrium and a heart ventricle is provided. The prosthetic valve is constrained from expansion during delivery and includes an annular valve body, a plurality of ventricular anchors, and a plurality of atrial anchors. The method includes releasing the plurality of ventricular anchors within the atrium. The method additionally includes releasing the plurality of atrial anchors within the atrium. The method additionally includes moving the released ventricular anchors through the mitral valve and into the ventricle. The method additionally includes after moving the released ventricular anchors from the atrium to the ventricle, releasing the annular valve body, thereby anchoring the prosthetic valve within the mitral valve.

The annular valve body is released within the ventricle. The ventricular anchors are released prior to release of the atrial anchors. The released ventricular anchors are moved into the ventricle prior to release of the atrial anchors. The atrial anchors are released prior to release of the ventricular anchors. The annular valve body is constrained from expansion during release of the ventricular anchors and atrial anchors and during movement of the ventricular anchors into the ventricle. Terminal ends of the ventricular anchors deflect radially outward relative to the annular valve body when the ventricular anchors are released. Terminal ends of the atrial anchors deflect radially outward relative to the annular valve body when the atrial anchors are released. The annular valve body radially expands when released. Release of the annular valve body causes the ventricular anchors and atrial anchors to clamp native valve tissue therebetween. An axial distance between the released atrial anchors and the released ventricular anchors is reduced during release of the annular valve body. The ventricular anchors and the atrial anchors shift radially outward when the annular valve body is released. The method additionally includes prior to release of the annular valve body, moving the released ventricular anchors in an atrial direction such that the ventricular anchors engage tissue of the native mitral valve. The ventricular anchors pull distinct portions of the native mitral valve together. Movement of the released ventricular anchors in the atrial direction occurs prior to release of the atrial anchors. Each ventricular anchor includes a connection point to the annular valve body. The connection points of the ventricular anchors form a first diameter during movement of the ventricular anchors into the ventricle, and a second diameter after release of the annular valve body, the second diameter being larger than the first diameter.

According to another exemplary embodiment of the present disclosure, a method of implanting an expandable prosthetic valve within a native mitral valve between an atrium and a ventricle is provided. The method includes outwardly moving terminal ends of ventricular anchors relative to a portion of an annular valve body positioned within the atrium. The method additionally includes after outwardly moving the terminal ends of the ventricular anchors, advancing at least a portion of the expandable prosthetic valve containing the ventricular anchors through the native mitral valve into the ventricle. The method additionally includes outwardly moving terminal ends of atrial anchors relative to a portion of the annular valve body while the atrial anchors are at least partially positioned within the atrium. The method additionally includes after outwardly moving the terminal ends of the ventricular anchors and outwardly moving the terminal ends of the atrial anchors, radially expanding the annular valve body, thereby anchoring native heart valve tissue between the atrial anchors and ventricular anchors.

The ventricular anchors and the atrial anchors are biased to assume expanded configurations and are constrained in non-expanded configurations. Outwardly moving the respective terminal ends of the ventricular anchors and the atrial anchors includes respectively releasing constraints on the ventricular anchors and the atrial anchors to thereby enable the ventricular anchors and the atrial anchors to spring outwardly. Expanding the annular valve body includes releasing the annular valve body from a constraint to thereby enable the annular valve body to expand to a pre-contraction expanded configuration. Expanding of the annular valve body anchors the prosthetic valve within the native mitral valve. The annular valve body is expanded within the ventricle. The method additionally includes prior to expanding the annular valve body, advancing the ventricular anchors in an atrial direction such that the ventricular anchors engage tissue of the native mitral valve.

Additional features and advantages of the disclosed embodiments will be set forth in part in the description that follows, and in part will be obvious from the description, or may be learned by practice of the disclosed embodiments. The features and advantages of the disclosed embodiments will be realized and attained by the elements and combinations particularly pointed out in the appended claims.

It is to be understood that both the foregoing general description and the following detailed description are examples and explanatory only and are not restrictive of the disclosed embodiments as claimed.

The accompanying drawings constitute a part of this specification. The drawings illustrate several embodiments of the present disclosure and, together with the description, serve to explain the principles of the disclosed embodiments as set forth in the accompanying claims.

BRIEF DESCRIPTION OF THE DRAWINGS

FIGS. 5A-5E illustrate structural changes in the exemplary frame of FIG. 2A during transitioning of the frame between a radially-contracted configuration and a radially-expanded configuration, consistent with various embodiments of the present disclosure.

DETAILED DESCRIPTION

Figure 1A:
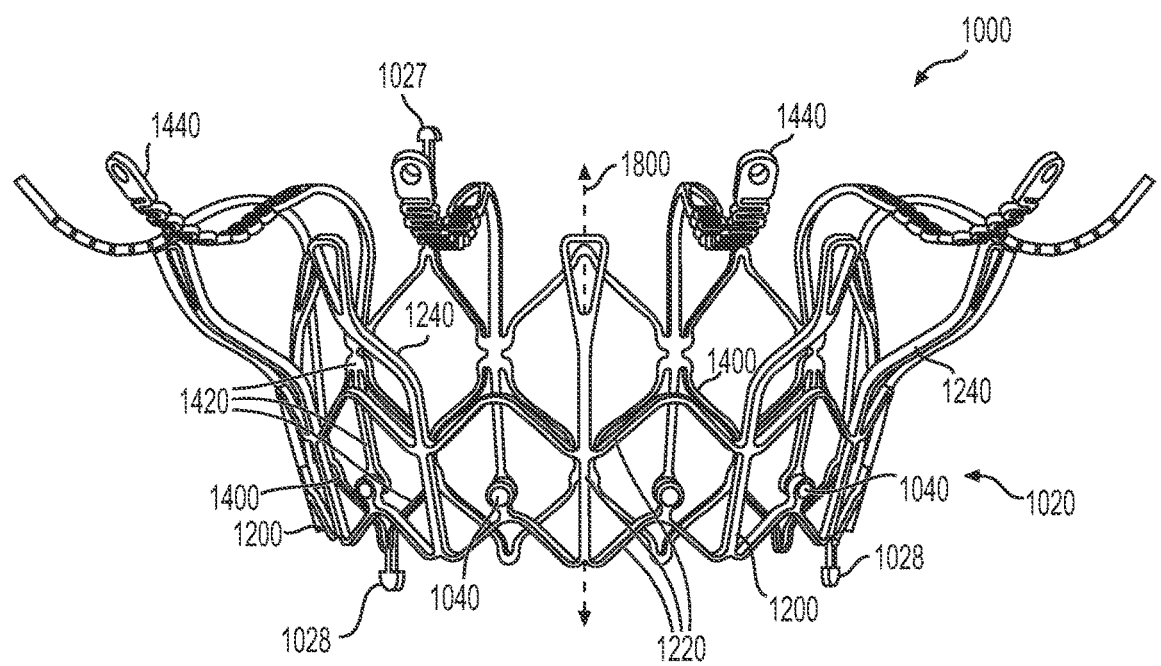
FIG. 1A illustrates a front elevation view of an exemplary frame for a prosthetic valve, consistent with various embodiments of the present disclosure.

Exemplary embodiments are described with reference to the accompanying drawings. In the figures, which are not necessarily drawn to scale, the left-most digit(s) of a reference number identifies the figure in which the reference number first appears. Wherever convenient, the same reference numbers are used throughout the drawings to refer to the same or like parts. While examples and features of disclosed principles are described herein, modifications, adaptations, and other implementations are possible without departing from the spirit and scope of the disclosed embodiments. Also, the words "comprising," "having," "containing," and "including," and other similar forms are intended to be equivalent in meaning and be open ended in that an item or items following any one of these words is not meant to be an exhaustive listing of such item or items, or meant to be limited to only the listed item or items. It should also be noted that as used in the present disclosure and in the appended claims, the singular forms "a," "an," and "the" include plural references unless the context clearly dictates otherwise.

In some embodiments of the present disclosure, an "atrial direction" may refer to a direction extending towards an atrium of the heart. For example, from a location within the left ventricle or the mitral valve, an atrial direction may refer to a direction extending towards the left atrium. Additionally, from a location within an atrium (e.g., the left atrium), an atrial direction may refer to a direction extending away from an adjacent atrioventricular valve (e.g., the mitral valve) and further into the atrium. For example, in FIGS. 10G and 10H, an atrial direction may refer to a direction extending upwards from prosthetic valve 6000 towards atrium 9010. In some exemplary embodiments, an atrial direction need not necessarily be parallel to a longitudinal axis of a prosthetic valve (e.g., longitudinal axis 2800 illustrated in FIG. 2A), so long as the direction is angled towards an atrium. The atrial direction may be parallel to a longitudinal axis of a prosthetic valve in some cases. In some embodiments, a "non-ventricular direction" may refer to a direction that does not extend towards a ventricle of the heart. A "non-ventricular direction" may extend in an atrial direction, or it may extend laterally in a direction perpendicular to a ventricular direction.

In some exemplary embodiments of the present disclosure, a "ventricular direction" may refer to a direction extending towards a ventricle of the heart. From a location within the left atrium or the mitral valve, a ventricular direction may refer to a direction extending towards the left ventricle. Additionally, from a location within a ventricle (e.g., the left ventricle), a ventricular direction may refer to a direction extending away from an adjacent atrioventricular valve (e.g., the mitral valve) and further into the ventricle. For example, in FIGS. 10G and 10H, a ventricular direction may refer to a direction extending downwards from prosthetic valve 6000 towards ventricle 9020. In some exemplary embodiments, a ventricular direction need not necessarily be parallel to a longitudinal axis of a prosthetic valve (e.g., longitudinal axis 2800 illustrated in FIG. 2A), so long as the direction is angled towards a ventricle. The ventricular direction may be parallel to a longitudinal axis of a prosthetic valve in some cases. In some embodiments, a "non-atrial direction" may refer to a direction that does not extend towards an atrium of the heart. A non-atrial direction may extend in a ventricular direction, or it may extend laterally in a direction perpendicular to an atrial direction.

Exemplary embodiments generally relate to prosthetic valves for implantation within a native valve and methods for implanting prosthetic valves within a native valve. In addition, exemplary embodiments generally relate to systems and methods for implantation of prosthetic valves by prosthetic valve delivery systems. While the present disclosure provides examples relating to prosthetic heart valves, and in particular prosthetic mitral valves, as well as delivery systems for prosthetic heart valves, it should be noted that aspects of the disclosure in their broadest sense are not limited to a prosthetic heart valve. Rather, the foregoing principles may be applied to other prosthetic valves as well. In various embodiments in accordance with the present disclosure, the term prosthetic valve refers generally to an implantable valve configured to restore and/or replace the functionality of a native valve, such as a diseased or otherwise impaired native heart valve.

An exemplary prosthetic valve may include a prosthetic valve configured to render a native valve structure non-functional, and may thus replace the function of the native valve. For example, an exemplary prosthetic valve may have a size and shape similar to the valve being replaced and may include a number of leaflet-like structures to regulate fluid flow and prevent backflow of blood through the valve. Additionally, or alternatively, an exemplary prosthetic valve may also include a prosthetic valve configured to leave the native valve structure intact and functional. An exemplary prosthetic valve may include a mitral valve, tricuspid valve, aortic valve, or pulmonary valve, as well as a valve outside of the heart, such as a venous valve, lymph node valve, ileocecal valve, or any other structure configured to control and/or regulate fluid flow in the body. An exemplary prosthetic valve may additionally or alternatively be configured to replace a failed bioprosthesis, such as a failed heart valve prosthesis.

Figure 1B:
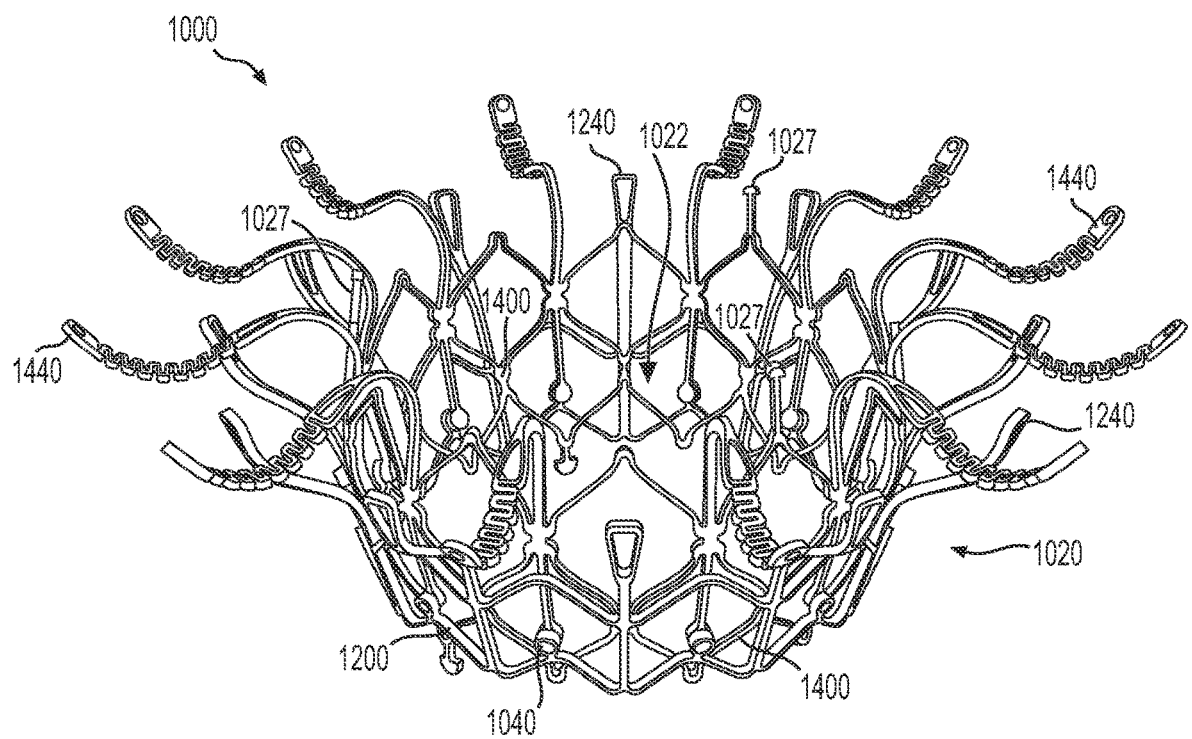
FIG. 1B illustrates a perspective view of the exemplary frame of FIG. 1A, consistent with various embodiments of the present disclosure.

FIG. 1A illustrates a front elevation view of an exemplary frame 1000 for a prosthetic valve. FIG. 1B illustrates a perspective view of frame 1000. Frame 1000 may be constructed of a shape memory material such as nickel titanium alloy (Nitinol) and may be configured to support other components of the prosthetic valve, such as prosthetic leaflets and protective cover layers. Frame 1000 may include an annular outer frame 1200 and an inner frame 1400 situated at least partially within the outer frame 1200. Annular outer frame 1200 and inner frame 1400 may be secured together by pins, screws, welding, soldering, adhesive, magnets, and/or any other suitable mechanism. For example, FIGS. 1A and 1B depict annular outer frame 1200 and inner frame 1400 connected by a plurality of connector pins 1040.

Annular outer frame 1200 may include an outer frame tubular portion 1220, which may be formed of a plurality of struts intersecting at junctions to form a wire mesh, stent-like, or cage-like structure of the outer frame tubular portion 1220. Annular outer frame 1200 may also include at least one ventricular anchoring leg 1240, which may be configured to extend radially outward from the outer frame tubular portion and which may contact, or otherwise engage, tissue within or near the native valve to anchor the prosthetic valve within the native valve. In some embodiments, exemplary valve frame 1000 may include twelve ventricular anchoring legs 1240, which may be configured to engage ventricular tissue of a native atrioventricular valve.

Inner frame 1400 may include an inner frame tubular portion 1420, which may be formed of a plurality of struts intersecting at junctions to form a wire mesh, stent-like, or cage-like structure of the inner frame tubular portion 1420. Inner frame 1400 may also include at least one atrial anchoring arm 1440, which may be configured to extend radially outward from the inner frame tubular portion and which may contact, or otherwise engage, tissue within or near the native valve to anchor the prosthetic valve within the native valve. In some embodiments, exemplary valve frame 1000 may include twelve atrial anchoring arms 1440, which may be configured to engage atrial tissue of a native atrioventricular valve.

Outer frame tubular portion 1220 and inner frame tubular portion 1420 may together form an annular valve body 1020 of the prosthetic valve, which may have at least one opening and from which the ventricular anchoring legs 1240 and atrial anchoring arms 1440 may extend. Annular valve body 1020 may include an axial lumen 1022 extending through the annular valve body 1020 along a longitudinal axis 1800 of the prosthetic valve. In some embodiments, annular valve body 1020 may be configured to receive a flow control device, such as one or more prosthetic leaflets, within axial lumen 1022. Optionally, annular valve body 1020 may include one or more atrial end delivery posts 1027 along an atrial end (i.e., top end) of the annular valve body and/or one or more ventricular end delivery posts 1028 along a ventricular end (i.e., bottom end) of the annular valve body. Delivery posts 1027 and 1028 may be configured to removably engage a delivery device of the prosthetic valve, for example, to assist with placement of frame 1000 within or near a native valve.

Figure 2A:
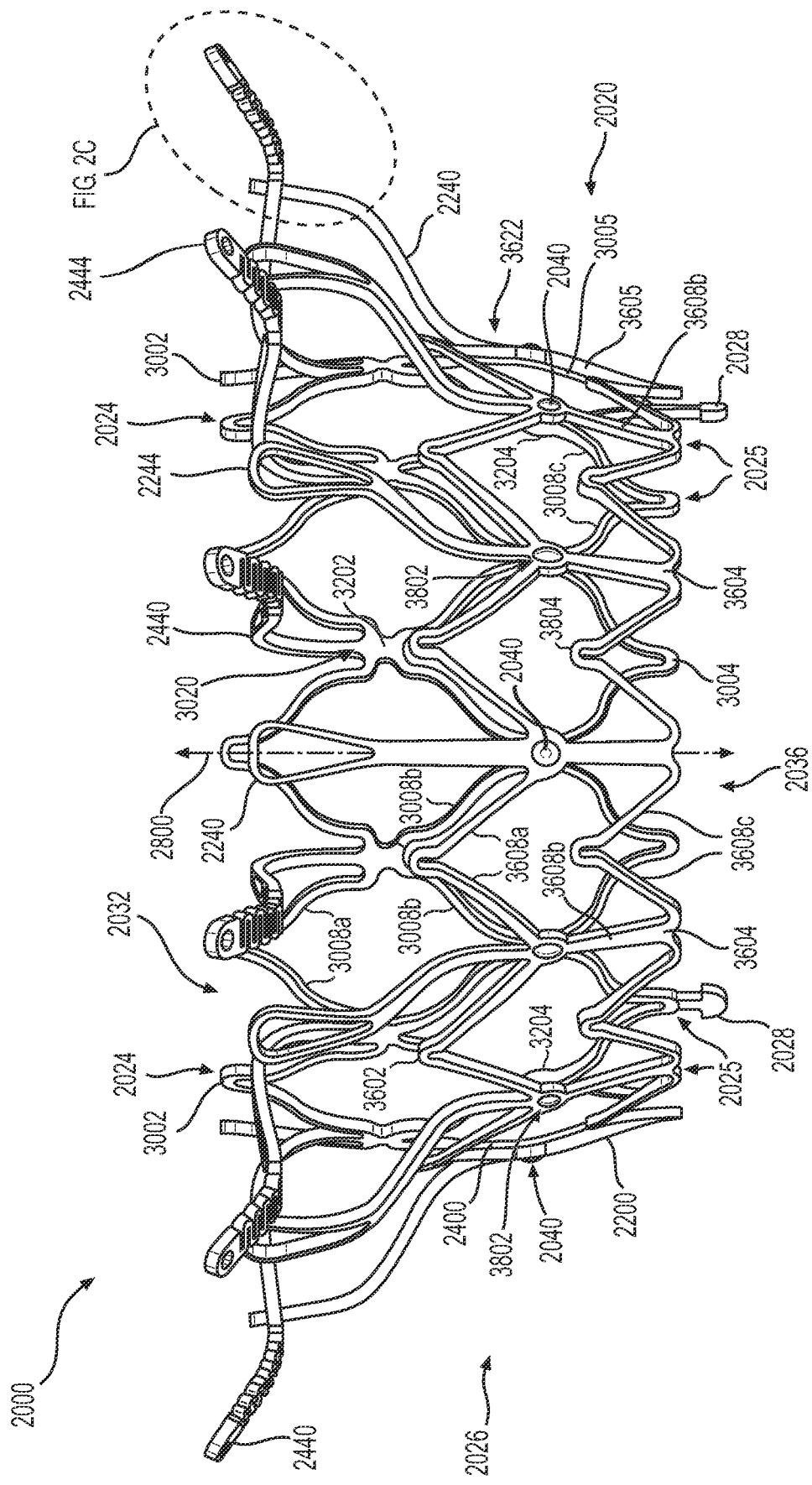
FIG. 2A illustrates a front elevation view of another exemplary frame for a prosthetic valve, consistent with various embodiments of the present disclosure.
Figure 2B:
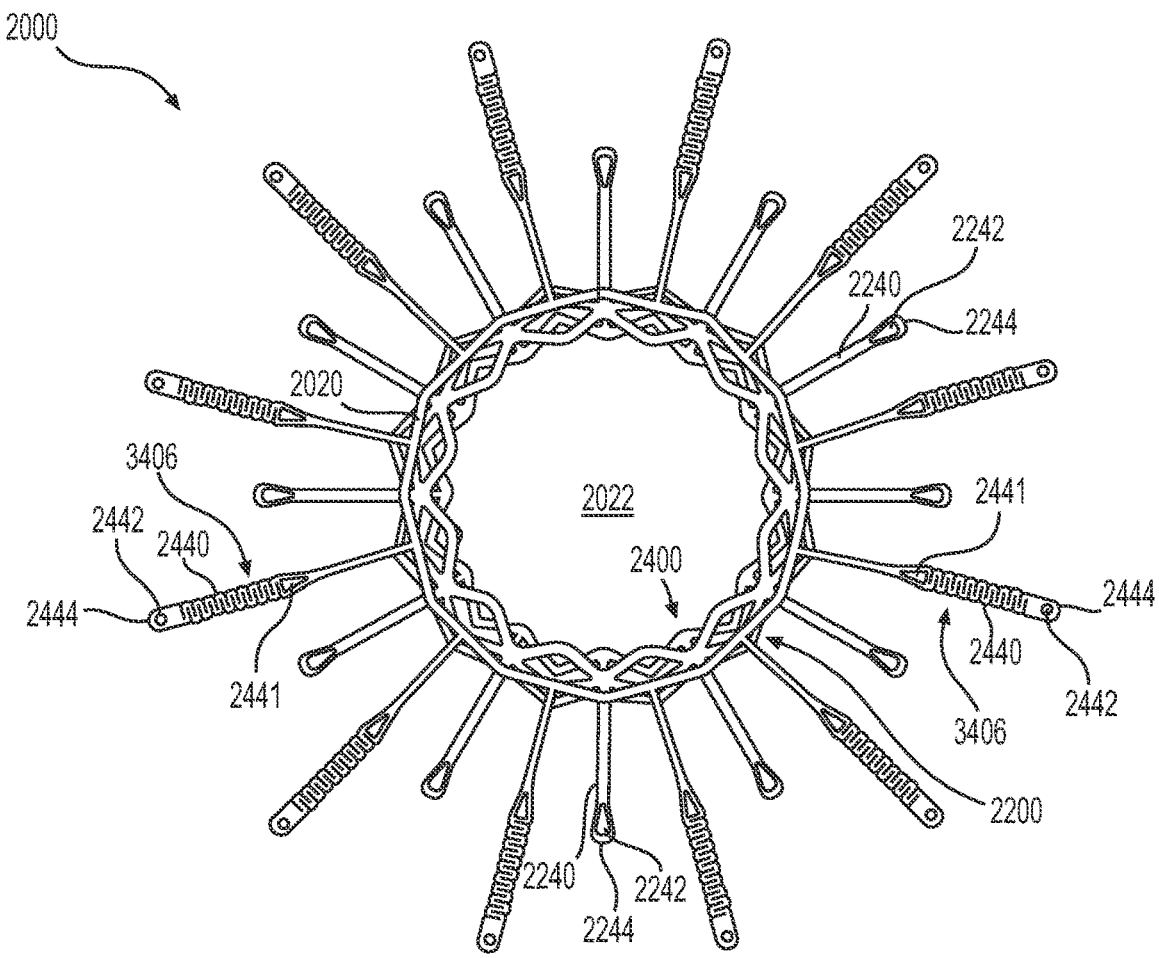
FIG. 2B illustrates a top plan view of the exemplary frame of FIG. 2A, consistent with various embodiments of the present disclosure.

FIG. 2A illustrates a front view of another exemplary frame 2000 for a prosthetic valve. FIG. 2B illustrates a top plan view of the frame 2000. Frame 2000 may include an annular outer frame 2200 and an inner frame 2400 situated at least partially within the annular outer frame 2200. Annular outer frame 2200 and inner frame 2400 may be secured together by pins, screws, welding, soldering, adhesive, magnets, and/or any other suitable mechanism. For example, FIGS. 2A and 2B depict annular outer frame 2200 and inner frame 2400 connected by a plurality of connector pins 2040.

Annular outer frame 2200 may include an outer frame tubular portion 3605, which may be formed of a plurality of struts intersecting at junctions to form a wire mesh, stent-like, or cage-like structure of the outer frame tubular portion 3605. For example, as illustrated in FIG. 2A, annular outer frame 2200 may include outer frame atrial circumferential struts 3608a, outer frame leg base struts 3608b, and outer frame ventricular circumferential struts 3608c intersecting at atrial end outer frame junctions 3602, leg attachment junctions 3802, outer frame junctions 3804, and ventricular end outer frame junctions 3604 to form outer frame tubular portion 3605. Annular outer frame 2200 may also include at least one ventricular anchoring leg 2240, which may extend from leg attachment junction 3802 of the outer frame tubular portion 3605 and which may be configured to engage ventricular tissue of a native valve to anchor the prosthetic valve in the native valve. The at least one ventricular anchoring leg 2240 may include a proximal leg end 3622, which may be the end of the leg connected to the outer frame tubular portion, and a distal leg end 2244, which may be situated radially outward from the outer frame tubular portion. As shown in FIG. 2B, the at least one ventricular anchoring leg 2240 may include at least one opening 2242.

Inner frame 2400 may include an inner frame tubular portion 3005, which may be formed of a plurality of struts intersecting at junctions to form a wire mesh, stent-like, or cage-like structure of the inner frame tubular portion 3005. For example, as illustrated in FIG. 2A, inner frame 2400 may include inner frame atrial struts 3008a, inner frame intermediate struts 3008b, and inner frame ventricular struts 3008c intersecting at atrial end inner frame junctions 3002, arm attachment junctions 3202, inner frame strut junctions 3204, and ventricular end inner frame junctions 3004 to form inner frame tubular portion 3005. Inner frame 2400 may also include at least one atrial anchoring arm 2440, which may extend from arm attachment junction 3202 of the inner frame tubular portion 3005 and which may be configured to engage atrial tissue of a native valve to anchor the prosthetic valve in the native valve. The at least one atrial anchoring arm 2440 may include a proximal arm end 3020, which may be the end of the arm connected to the inner frame tubular portion, and a distal arm end 2444, which may be situated radially outward from the inner frame tubular portion. As shown in FIG. 2B, the at least one atrial anchoring arm 2440 may include a proximal arm opening 2441 and a distal arm opening 2442.

Outer frame tubular portion 3605 and inner frame tubular portion 3005 may together form an annular valve body 2020 of the prosthetic valve, which may have at least one opening and from which the ventricular anchoring legs 2240 and atrial anchoring arms 2440 may extend. Annular valve body 2020 may include an axial lumen 2022 extending through the annular valve body 2020 along a longitudinal axis 2800 of the prosthetic valve. Annular valve body 2020 may have an atrial end 2024, a ventricular end 2025 opposite the atrial end, and an intermediate portion 2026 extending between the atrial and ventricular ends. In some embodiments, the atrial end may refer to the portion of the annular valve body configured to be situated at a location within the atrium that is furthest from an adjacent ventricle, when the prosthetic valve is implanted in a native valve. Similarly, the ventricular end may refer to the portion of the annular valve body configured to be situated at a location within the ventricle that is furthest from an adjacent atrium, when the prosthetic valve is implanted in a native valve. The intermediate portion 2026 may extend between the atrial end 2024 and ventricular end 2025. In some embodiments, annular valve body 2020 may include one or more ventricular end delivery posts 1028 along the ventricular end 2025 of the annular valve body. Axial lumen 2022 may include an inlet opening 2032 at the atrial end of the annular valve body, as well as an outlet opening 2036 at the ventricular end of the annular valve body.

Figure 2C:
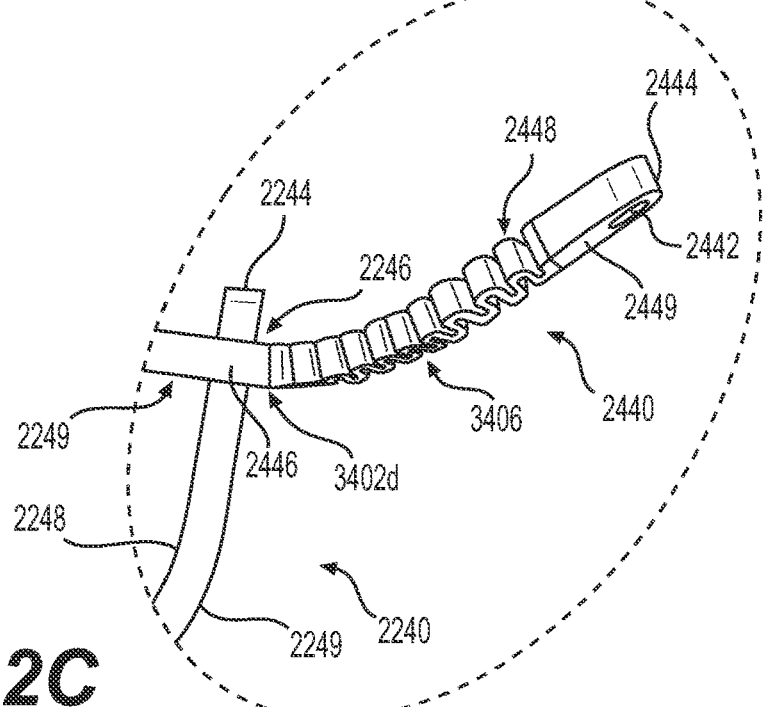
FIG. 2C illustrates an enlarged view of an atrial anchoring arm and a ventricular anchoring leg of the exemplary frame of FIG. 2A, consistent with various embodiments of the present disclosure.

FIG. 2C illustrates an enlarged view of an atrial anchoring arm 2440 and a ventricular anchoring leg 2240 of frame 2000. Ventricular anchoring leg 2240 may include an inner, atrially-facing leg surface 2248 and an outer, ventricularly-facing leg surface 2249. Atrial anchoring arm 2440 may include an atrially-facing arm surface 2448 and a ventricularly-facing arm surface 2449. In some embodiments, atrial anchoring arm 2440 may include an arm portion 2446 configured to be arranged in a common lateral plane with leg portion 2246 of the ventricular anchoring leg 2240. That is, leg portion 2246 and arm portion 2446 may be positioned at the same axial position along longitudinal axis 2800.

Figure 2D:
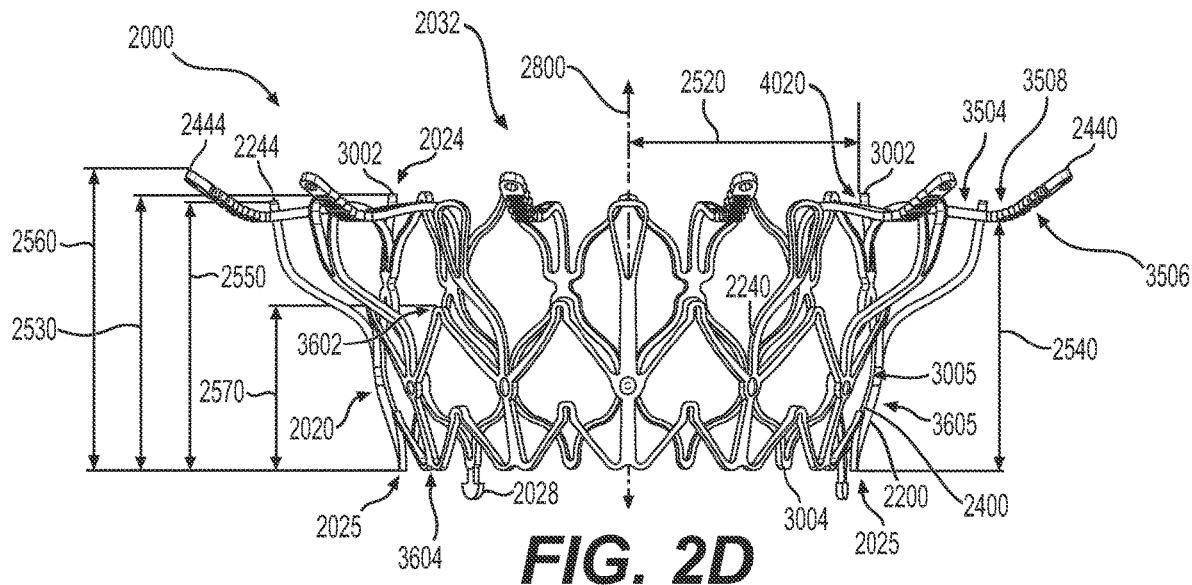
FIG. 2D illustrates another front elevation view of the exemplary frame of FIG. 2A, consistent with various embodiments of the present disclosure.

FIG. 2D illustrates another front elevation view of frame 2000. The exemplary prosthetic valve, as well as frame 2000, may have an axial height 2560, which may extend between terminal arm ends 2444 and ventricular end 2025 of the annular valve body. Inner frame tubular portion 3005 may have an axial height 2530, which may extend between atrial end inner frame junctions 3002 and ventricular end inner frame junctions 3004. Annular outer frame 2200 may have an axial height 2550, which may extend between terminal leg ends 2244 and ventricular end 2025 of the annular valve body. Outer frame tubular portion 3605 may have an axial height 2570, which may extend between atrial end outer frame junctions 3602 and ventricular end outer frame junctions 3604. In some embodiments, frame 2000 may have a ventricular device protrusion distance 2540, which may represent the distance over which the prosthetic valve protrudes into a left ventricle when the prosthetic valve is implanted in a native mitral valve. Annular valve body 2020 may include a valve inlet radius 2520, which may be the radius of atrial inlet opening 2032.

Figure 2E:
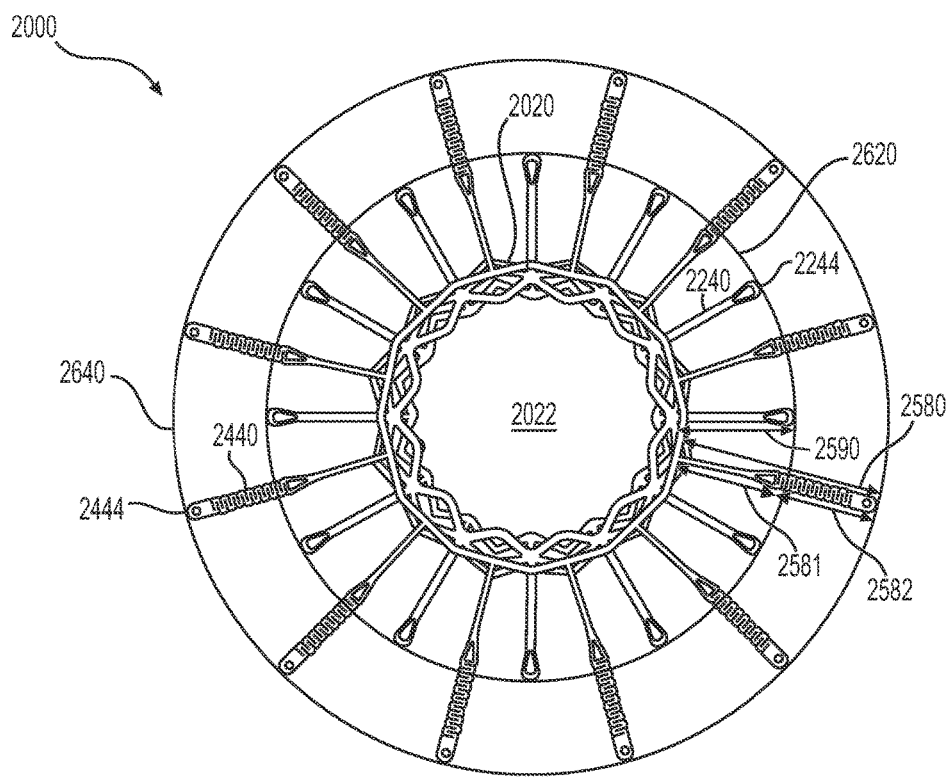
FIG. 2E illustrates another top plan view of the exemplary frame of FIG. 2A, consistent with various embodiments of the present disclosure.

FIG. 2E illustrates another top plan view of frame 2000. The atrial anchoring arms 2440 may have a length 2580, and the ventricular anchoring legs 2240 may have a length 2590. The terminal arm ends 2444 may define an atrial anchoring arm circumference 2640. The terminal leg ends 2244 may define a ventricular anchoring leg circumference 2620, which may be concentric with atrial anchoring arm circumference 2640. Inflexible portions 3402 of the atrial anchoring arms (illustrated in FIG. 3B) may have a length 2581. Serpentine structures 3406 of the atrial anchoring arms (illustrated in FIG. 3B) may have a length 2582.

Figure 3A:
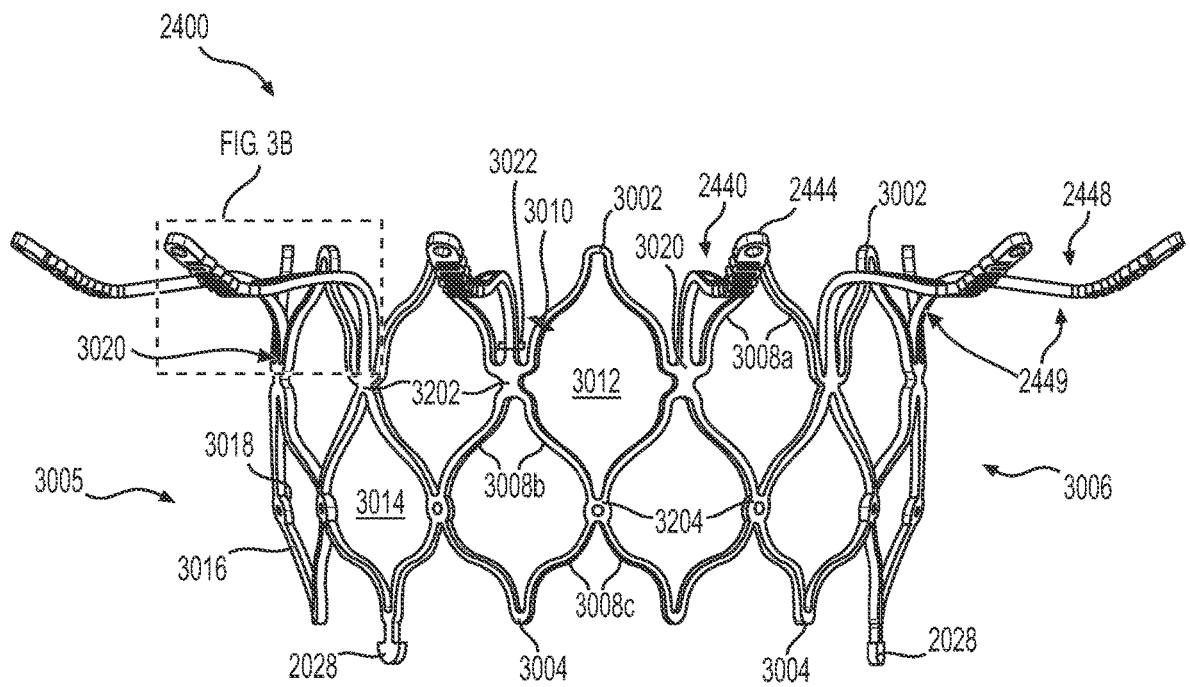
FIG. 3A illustrates a front elevation view of an inner frame of the exemplary frame of FIG. 2A, consistent with various embodiments of the present disclosure.

FIG. 3A illustrates a front elevation view of inner frame 2400. The atrial end inner frame junctions 3002 and ventricular end inner frame junctions 3004 may form the atrial end and ventricular end, respectively, of inner frame 2400. Inner frame intermediate portion 3006 may extend between atrial end inner frame junctions 3002 and ventricular end inner frame junctions 3004. Inner frame tubular portion 3005 may have a radially inner surface 3018 and a radially outer surface 3016. Inner frame atrial struts 3008a and inner frame intermediate struts 3008b may intersect at atrial end inner frame junctions 3002, arm attachment junctions 3202, and strut junctions 3204 to form a first, atrial row of closed cells 3012. Inner frame intermediate struts 3008b and inner frame ventricular struts 3008c may intersect at arm attachment junctions 3202, strut junctions 3204, and ventricular end inner frame junctions 3004 to form a second, ventricular row of closed cells 3014. At least one inner frame atrial strut 3008a may have a cross-sectional area 3010. At least one atrial anchoring arm 2440 may have a cross-sectional area 3022.

Figure 3B:
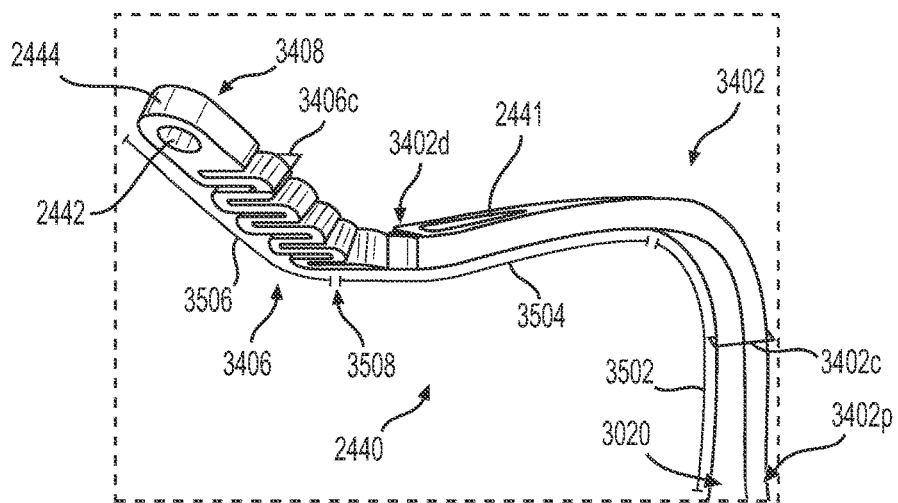
FIG. 3B illustrates an enlarged view of an atrial anchoring arm of the exemplary inner frame of FIG. 3A, consistent with various embodiments of the present disclosure.

FIG. 3B illustrates an enlarged view of an atrial anchoring arm 2440 of inner frame 2400. Atrial anchoring arm 2440 may include a proximal arm portion 3502 configured to extend in an atrial direction, intermediate arm portion 3504 configured to extend in a ventricular direction, and distal arm portion 3506 configured to extend in an atrial direction. Arm transition portion 3508 may represent the transition between intermediate arm portion 3504 and distal arm portion 3506. Atrial anchoring arm 2440 may also include an inflexible portion 3402 extending to proximal arm end 3020, as well as a serpentine structure 3406, which may be situated radially external to the inflexible portion 3402. Inflexible portion 3402 may have a proximal end 3402p, a distal end 3402d, and a cross-sectional area 3402c. Serpentine structure 3406 may have a cross-sectional area 3406c. In some embodiments, atrial anchoring arm 2440 may include a terminal arm region 3408 situated radially external to serpentine structure 3406. Distal arm opening 2442 may be situated within terminal arm region 3408.

Figure 3C:
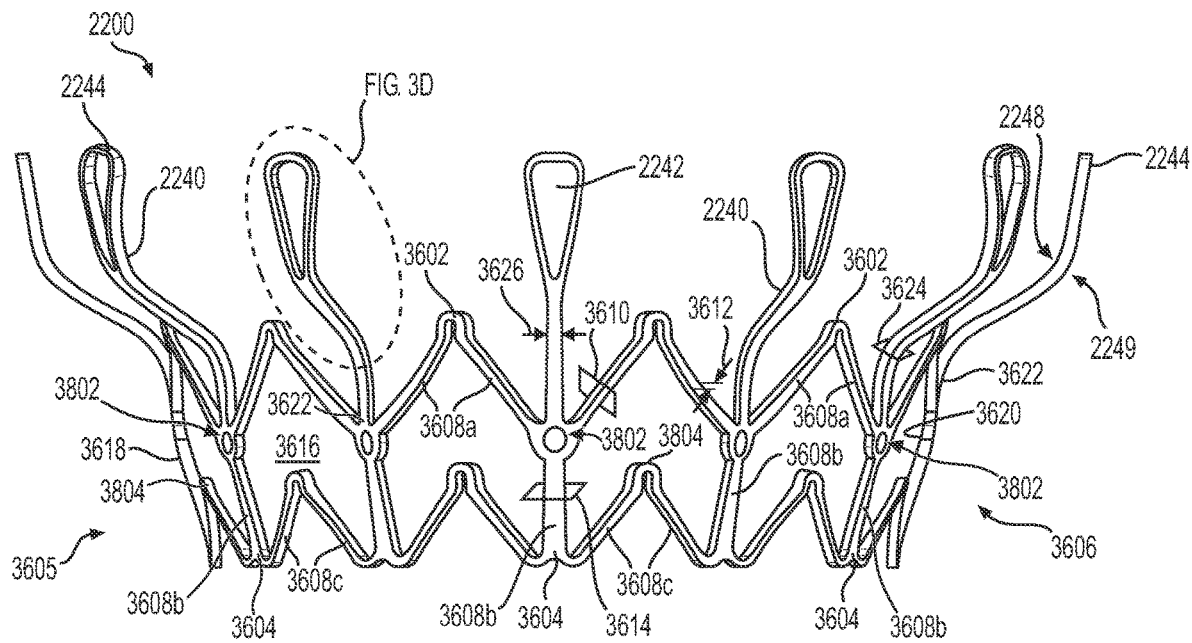
FIG. 3C illustrates a front elevation view of an outer frame of the exemplary frame of FIG. 2A, consistent with various embodiments of the present disclosure.

FIG. 3C illustrates a front elevation view of outer frame 2200. The atrial end outer frame junctions 3602 and ventricular end outer frame junctions 3604 may form the atrial end and ventricular end, respectively, of annular outer frame 2200. Outer frame intermediate portion 3606 may extend between atrial end outer frame junctions 3602 and ventricular end outer frame junctions 3604. Outer frame tubular portion 3605 may have a radially outer surface 3618 and a radially inner surface 3620. The outer frame atrial circumferential struts 3608a, outer frame leg base struts 3608b, and outer frame ventricular circumferential struts 3608c may intersect at the atrial end outer frame junctions 3602, leg attachment junctions 3802, outer frame junctions 3804, and ventricular end outer frame junctions 3604 to form closed cells 3616. At least one outer frame atrial circumferential strut 3608a may have a cross-sectional area 3610 and a width 3612. At least one outer frame leg base strut 3608b may have a cross-sectional area 3614. At least one ventricular anchoring leg may have a cross-sectional area 3624 and a radially outer surface width 3626.

Figure 3D:
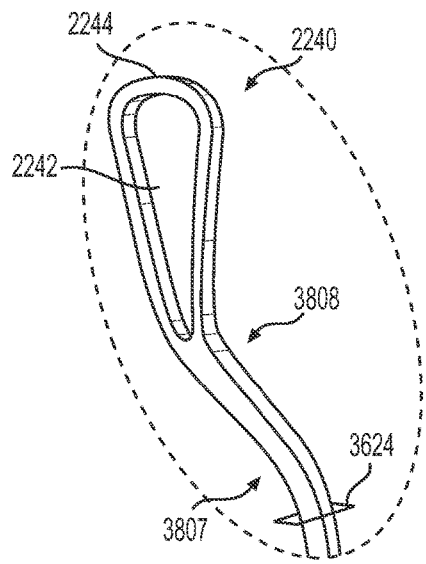
FIG. 3D illustrates an enlarged view of a ventricular anchoring leg of the exemplary outer frame of FIG. 3C, consistent with various embodiments of the present disclosure.

FIG. 3D illustrates an enlarged view of a portion of a ventricular anchoring leg 2240 of annular outer frame 2200. Ventricular anchoring leg 2240 may include a first, proximal curved portion 3807 and a second, distal curved portion 3808. In some embodiments, proximal curved portion 3807 may face radially outward. Additionally, or alternatively, distal curved portion 3808 may face radially inwards.

Figure 4B:
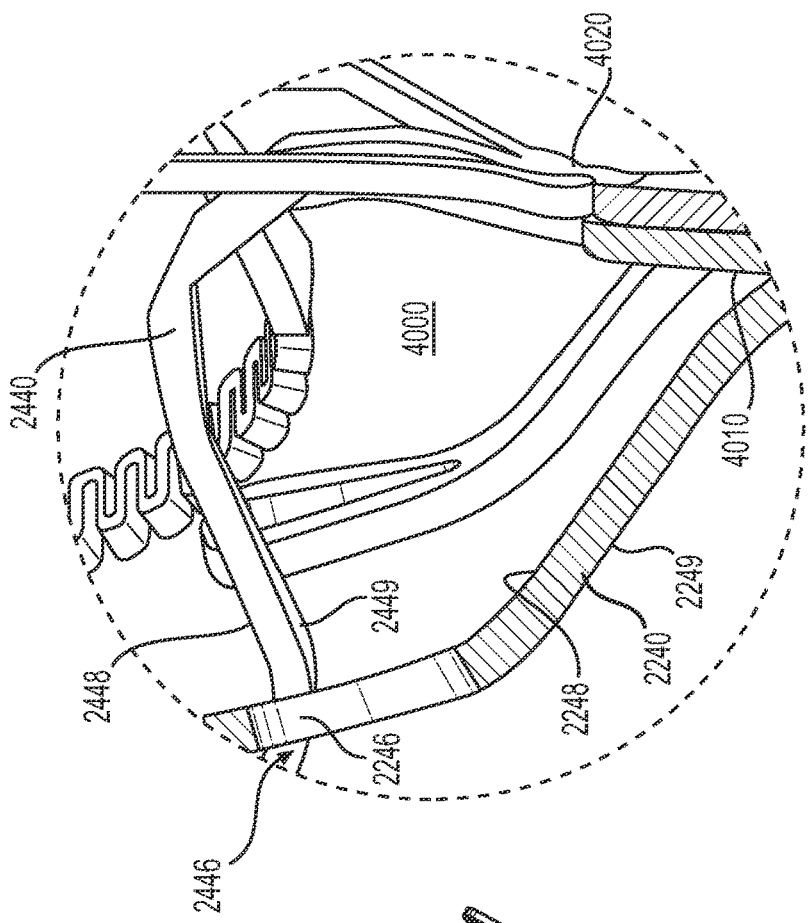
FIG. 4B illustrates an enlarged view of a volume between an atrial anchoring arm and a ventricular anchoring leg of the exemplary frame of FIG. 4A, consistent with various embodiments of the present disclosure.
Figure 4A:
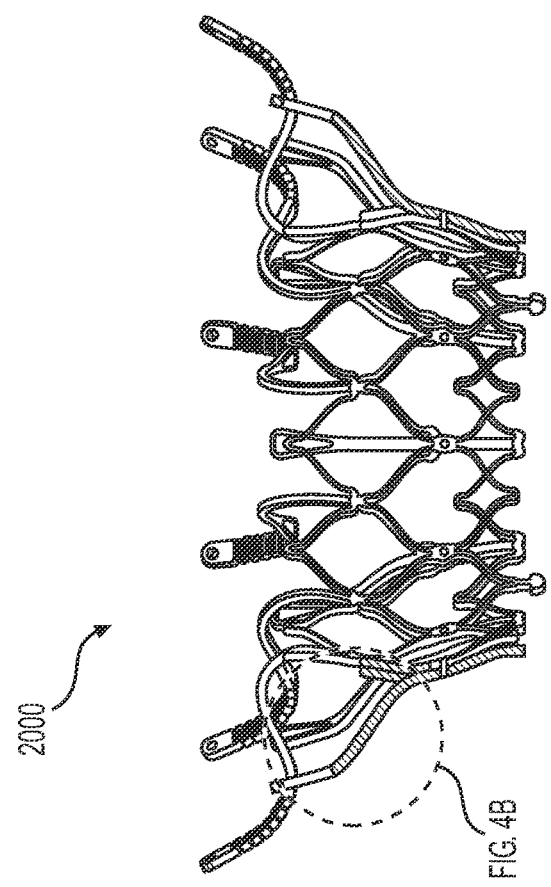
FIG. 4A illustrates a cross-sectional view of the exemplary frame of FIG. 2A, consistent with various embodiments of the present disclosure.

FIG. 4A illustrates a cross-sectional view of frame 2000, and FIG. 4B illustrates an enlarged view of a portion of FIG. 4A depicting a volume 4000 formed between the atrial anchoring arms 2440 and ventricular anchoring legs 2240. FIG. 4B also depicts an outer surface 4010 and inner surface 4020 of annular valve body 2020. In some embodiments, volume 4000 may be bounded by the ventricularly-facing surfaces 2449 of atrial anchoring arms 2440, by the inner, atrially-facing surfaces 2248 of ventricular anchoring legs 2240, and by the outer surface 4010 of the annular valve body 2020.

FIG. 5A illustrates a configuration of the exemplary prosthetic valve in which annular valve body 2020, atrial anchoring arms 2440, and ventricular anchoring legs 2240 are arranged in a radially-contracted configuration. In some embodiments, the configuration illustrated in FIG. 5A may constitute a radially-contracted configuration of the prosthetic valve.

FIG. 5B illustrates a configuration of the exemplary prosthetic valve in which annular valve body 2020 and atrial anchoring arms 2440 are arranged in a radially-contracted configuration. In the configuration of FIG. 5B, the ventricular anchoring legs 2240 may deflect radially outward away from annular valve body 2020, into a radially-expanded configuration of the ventricular anchoring legs 2240.

FIG. 5C illustrates a configuration of the exemplary prosthetic valve in which annular valve body 2020 and ventricular anchoring legs 2240 are arranged in a radially-contracted configuration. In the configuration of FIG. 5C, the atrial anchoring arms 2440 may deflect radially outward away from annular valve body 2020, into a radially-expanded configuration of the atrial anchoring arms 2440.

FIG. 5D illustrates a configuration of the exemplary prosthetic valve in which the atrial anchoring arms 2440 and ventricular anchoring legs 2240 may deflect radially outward away from annular valve body 2020 into their respective radially-expanded configurations, while annular valve body 2020 remains in a radially-contracted configuration. In the configuration of FIG. 5D, an axial distance 5004 may be formed between the atrial anchoring arms 2440 and the terminal ends 2244 of the ventricular anchoring legs 2240.

FIG. 5E illustrates a configuration of the exemplary prosthetic valve in which annular valve body 2020, atrial anchoring arms 2440, and ventricular anchoring legs 2240 are arranged in a radially-expanded configuration. In some embodiments, the configuration illustrated in FIG. 5E may constitute a radially-expanded configuration of the prosthetic valve.

Figure 6A:
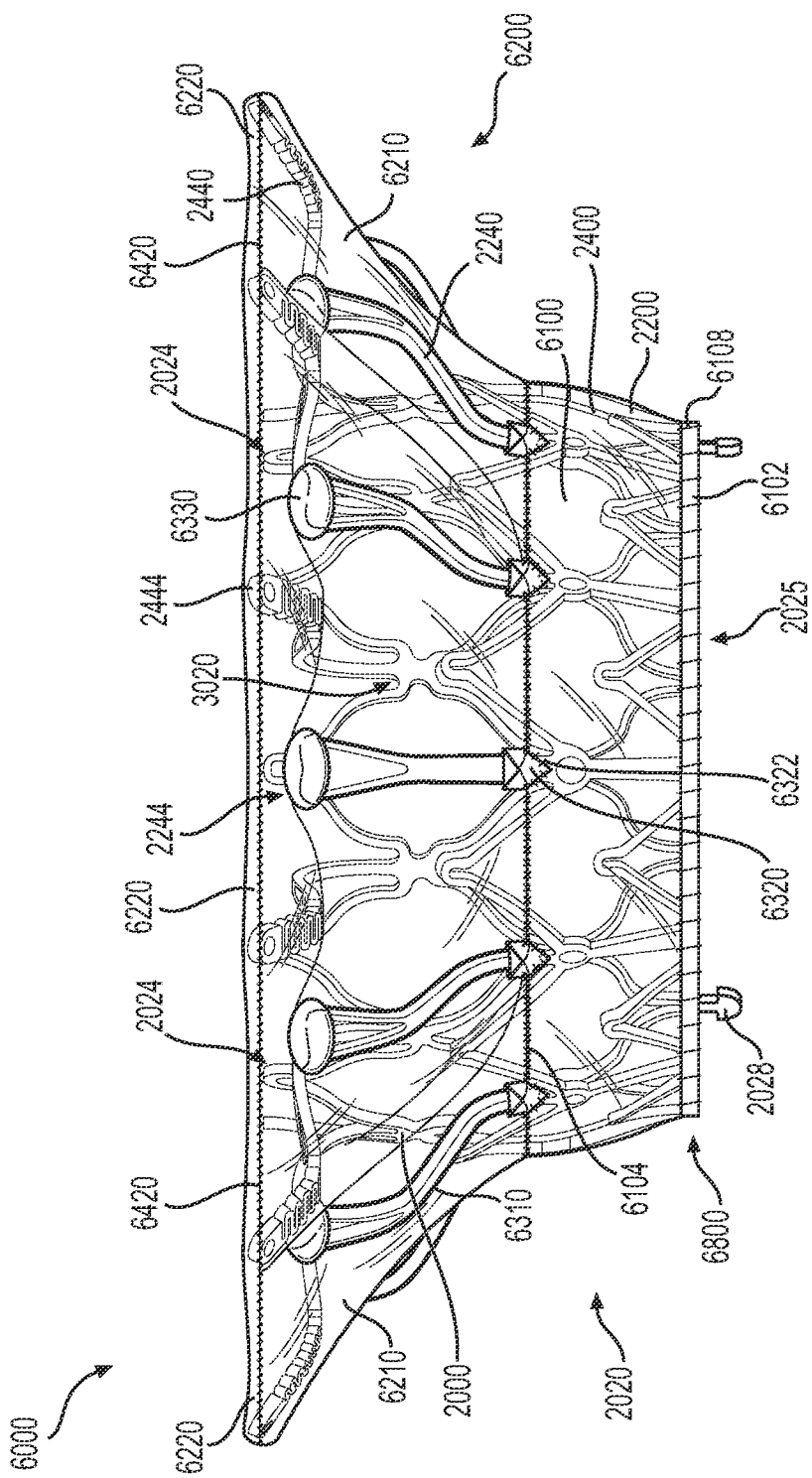
FIG. 6A illustrates a front elevation view of an exemplary prosthetic valve, consistent with various embodiments of the present disclosure.

FIG. 6A illustrates a front elevation view of prosthetic valve 6000. In some embodiments, prosthetic valve 6000 may be assembled upon frame 2000. Prosthetic valve 6000 may be configured for implantation within or near a native valve structure and may be configured to restore and/or replace the functionality of a native valve, such as a diseased or otherwise impaired native valve. Prosthetic valve 6000 may include valve frame 2000, including annular valve body 2020, the atrial anchoring arms 2440, and the ventricular anchoring legs 2240. Prosthetic valve 6000 may also include a skirt layer 6100 configured around an external surface of a portion of the annular valve body. Prosthetic valve 6000 may additionally include a first cuff sheet 6210, which may be connected to skirt layer 6100 via stitching 6104, as well as a second cuff sheet 6220, which may be connected to first cuff sheet 6210 via stitching 6420. In some embodiments, the first cuff sheet 6210 and second cuff sheet 6220 by extend around the terminal ends 2444 of the atrial anchoring arms 2440. Skirt layer 6100, first cuff sheet 6210, and second cuff sheet 6220 may be constructed of fluid-impermeable material and may accordingly be configured to prevent passage of blood or other fluids through portions of the prosthetic valve 6000 outside of the axial lumen 2022.

In some embodiments, prosthetic valve 6000 may additionally include a protective sleeve 6102 wrapped around the rim 6800 of the ventricular outlet opening of annular valve body 2020; protective sleeve 6102 may be secured to annular valve body 2020 by stitching 6108. Additionally, or alternatively, prosthetic valve 6000 may include at least one liner 6310 extending around an external surface of the ventricular anchoring legs 2240, with at least one protective layer 6330 positioned around the distal leg ends 2244 and at least one protective covering 6320 wrapped around the proximal leg ends 3622. In some embodiments, the at least one protective covering 6320 may be secured to the skirt layer 6100 via stitching 6322.

Figure 6B:
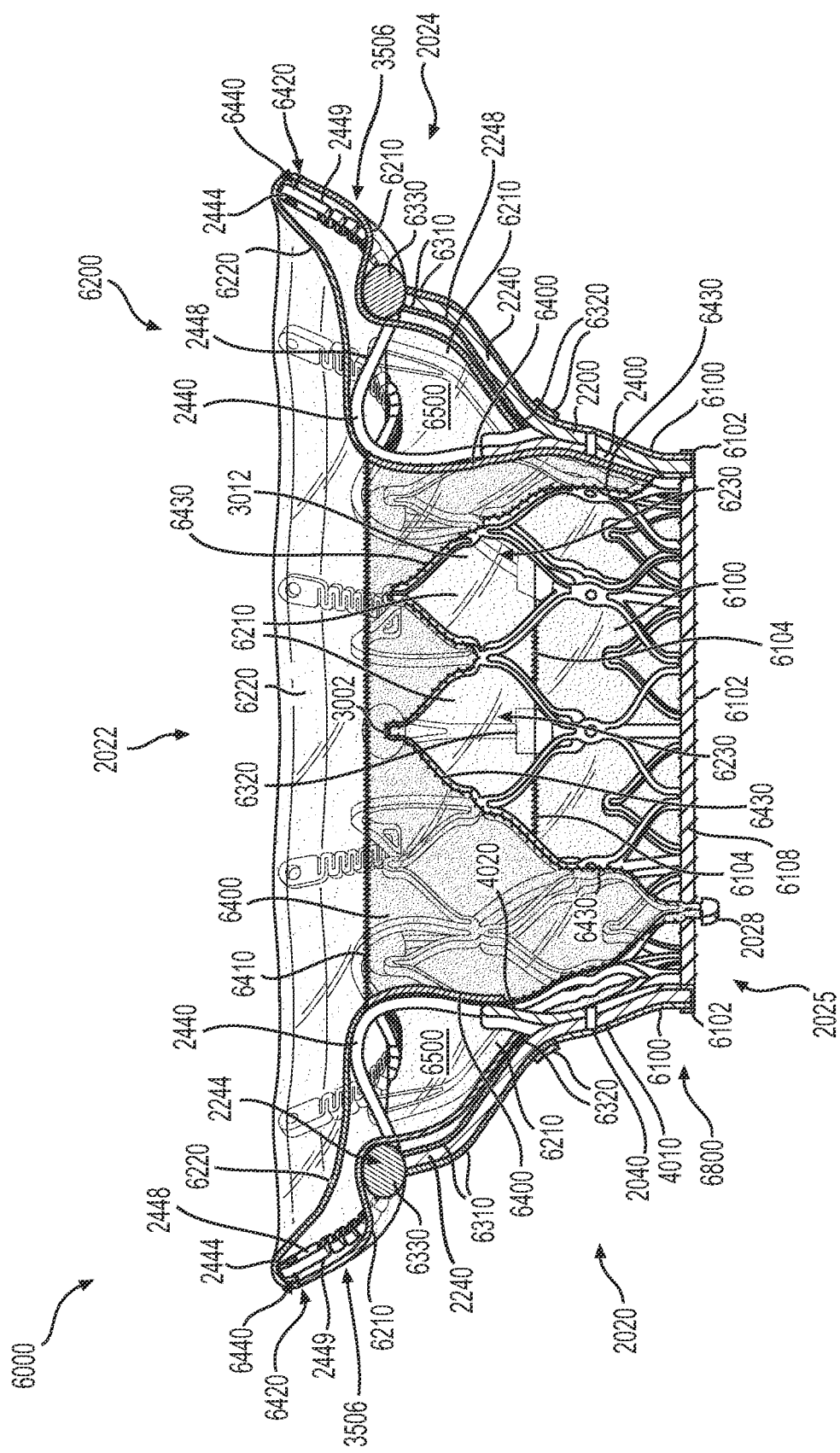
FIG. 6B illustrates a cross-sectional view of the exemplary prosthetic valve of FIG. 6A without leaflets, consistent with various embodiments of the present disclosure.

FIG. 6B illustrates a cross-sectional view of prosthetic valve 6000, without prosthetic leaflets situated within the axial lumen 2022. As illustrated in FIG. 6B, prosthetic valve 6000 may additionally include a liner 6400 covering at least a portion of the inner surface 4020 of the annular valve body 2020. Liner 6400 may be secured to the annular valve body 2020 via stitching 6430 and to the second cuff sheet 6220 via stitching 6410. First cuff sheet 6210, second cuff sheet 6220, and inner liner 6400 may together form an inflatable cuff 6200 having an interior volume 6500. In some embodiments, inflatable cuff 6200 may be secured to atrial anchoring arm 2440 via connector 6440. Blood may enter the cuff 6200 through openings 6230, causing the cuff 6200 to inflate radially outwards and axially in an atrial direction. In some embodiments, cuff 6200 may inflate radially outwards and press against tissue of the native valve. This engagement between the cuff and tissue of the native valve may form a barrier to flow of blood and other fluids around the outer circumference of the prosthetic valve 6000.

Figure 6C:
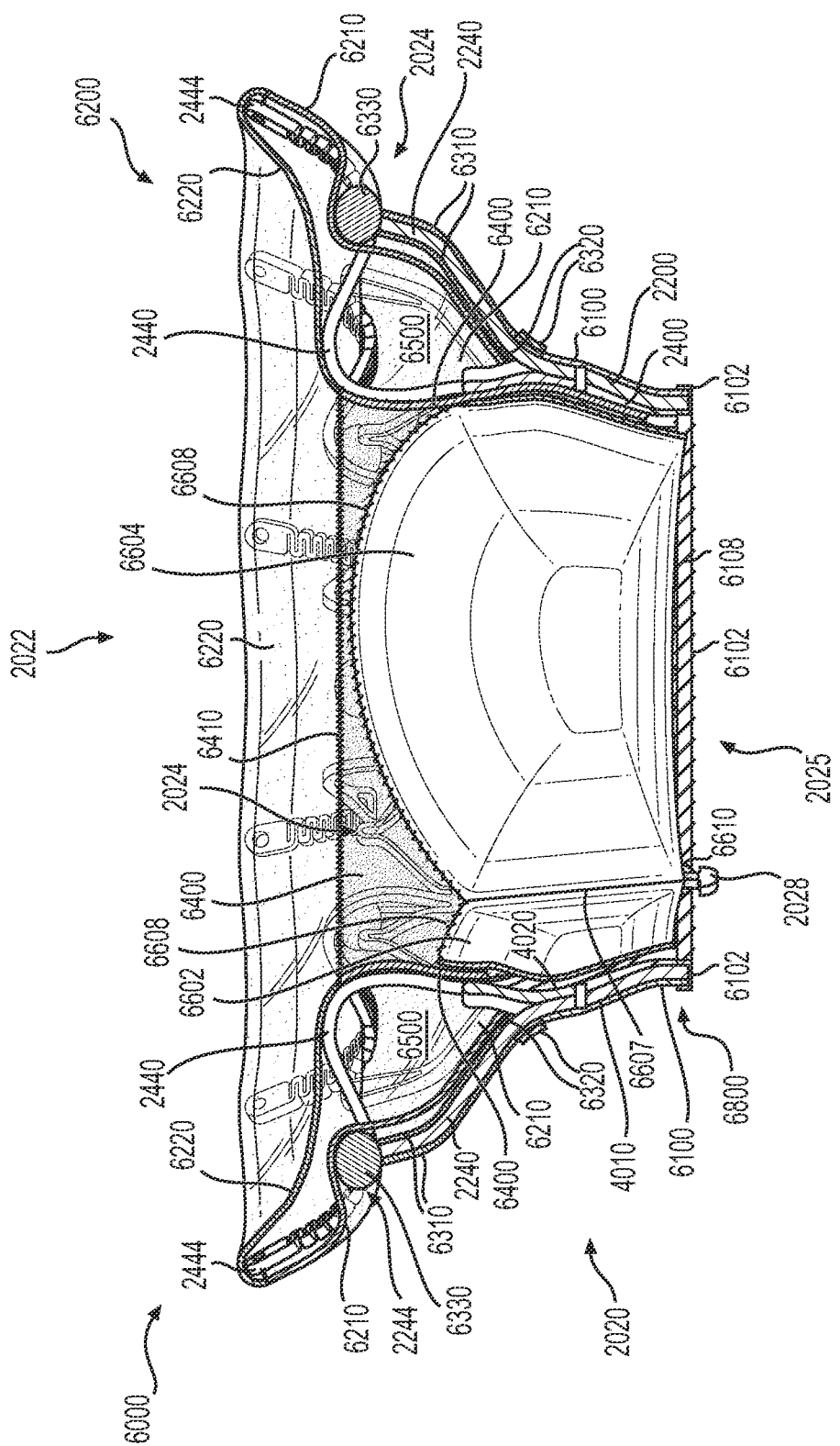
FIG. 6C illustrates a cross-sectional view of the exemplary prosthetic valve of FIG. 6A with leaflets, consistent with various embodiments of the present disclosure.

FIG. 6C illustrates a cross-sectional view of prosthetic valve 6000 with prosthetic leaflets 6602 and 6604 situated within the axial lumen 2022. In some embodiments, prosthetic valve 6000 may also include a third prosthetic leaflet 6606, which may not be visible in the view of FIG. 6C. The leaflets 6602, 6604, and 6606 may be secured to inner liner 6400 via stitching 6608 and may include a connector 6610 wrapping around the ventricular end delivery posts 2028 to secure the leaflets 6602, 6604, and 6606 to the valve frame 2000.

Figure 6D:
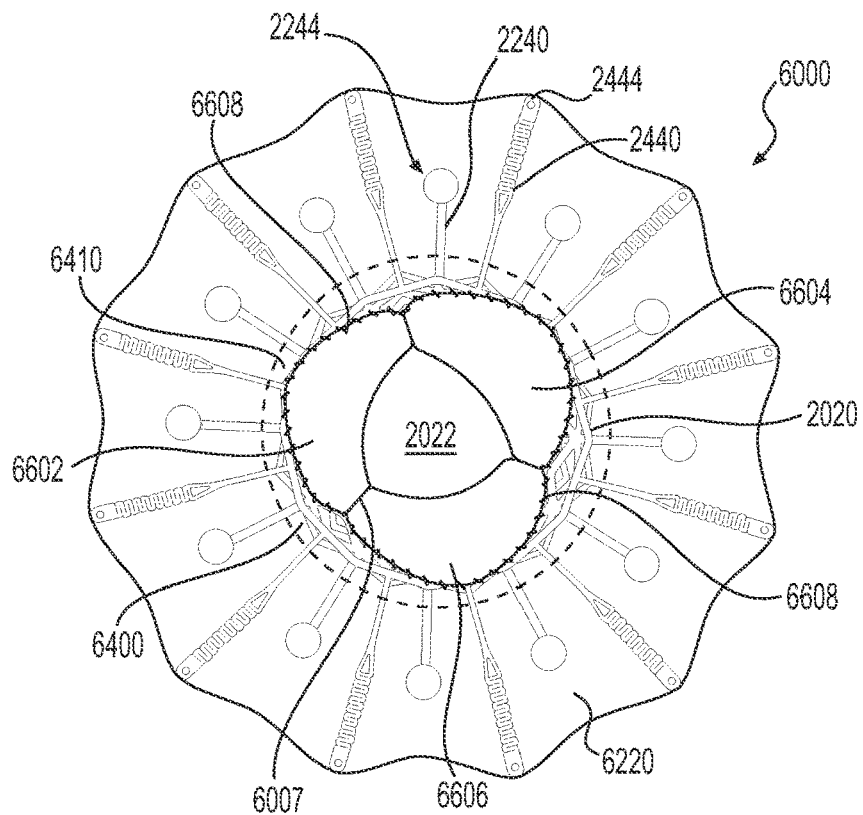
FIG. 6D illustrates a top plan view of the exemplary prosthetic valve of FIG. 6A with uninflated leaflets, consistent with various embodiments of the present disclosure.
Figure 6E:
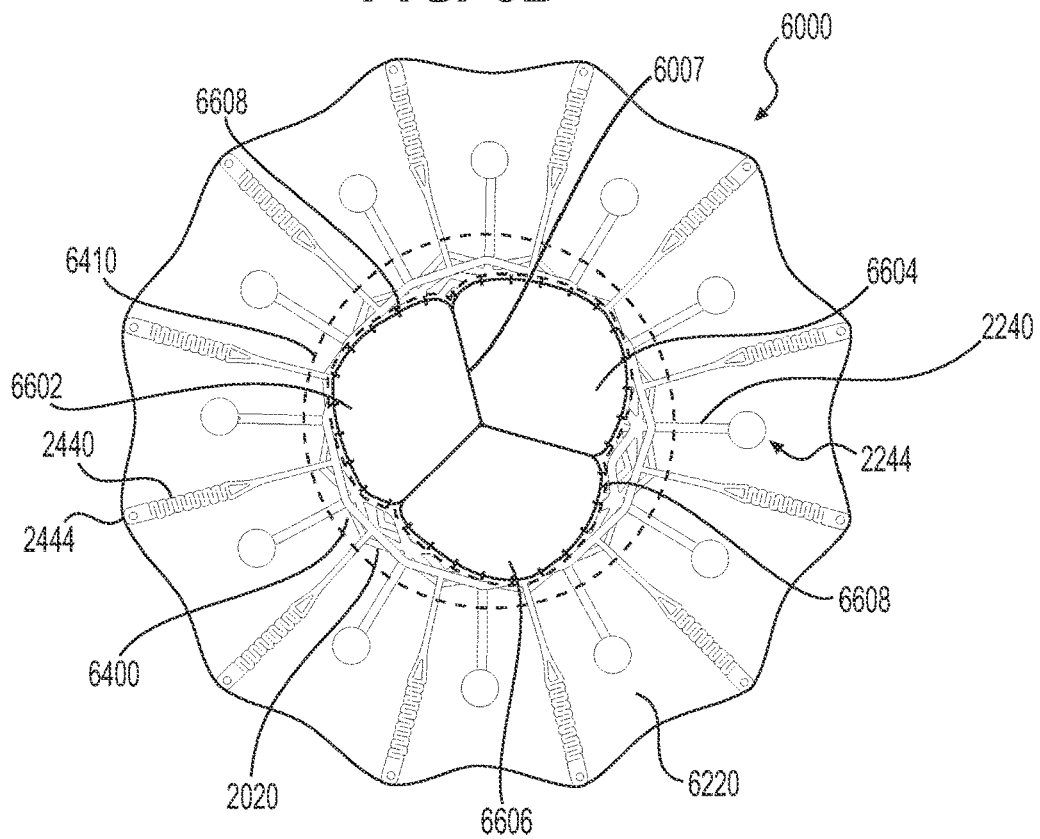
FIG. 6E illustrates a top plan view of the exemplary prosthetic valve of FIG. 6A with inflated leaflets, consistent with various embodiments of the present disclosure.

FIG. 6D illustrates a top plan view of prosthetic valve 6000, with leaflets 6602, 6604, and 6606 arranged in an open, uninflated configuration. In the open configuration, a space may be formed in the middle of the leaflets, permitting fluid to pass through the axial lumen 2022 of the prosthetic valve 6000. FIG. 6E illustrates a top plan view of prosthetic valve 6000, with leaflets 6602, 6604, and 6606 arranged in a closed, coapted configuration. In the closed configuration, the leaflets may press together such that the opening between them is closed. For example, the point of contact 6007 between two adjacent leaflets may extend to the center of the axial lumen; as a result, the leaflets may block fluid passage through the axial lumen 2022 of the prosthetic valve 6000.

Figure 7A:
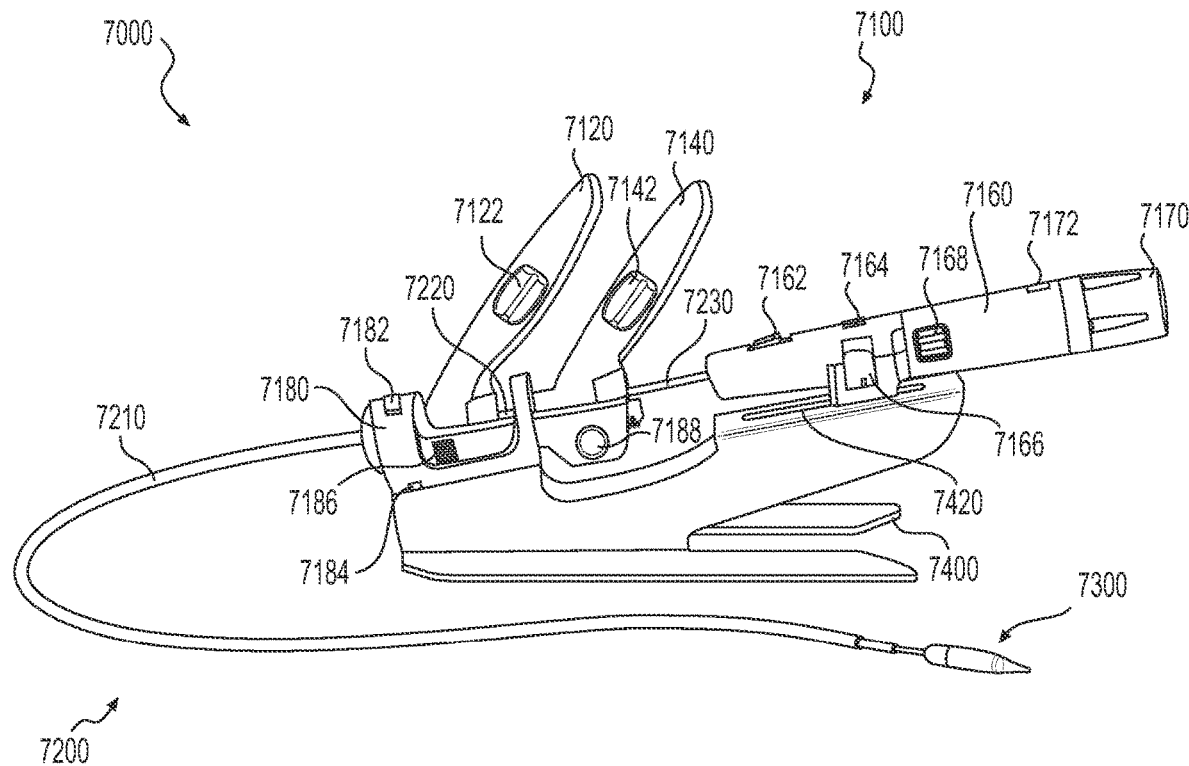
FIG. 7A illustrates an exemplary prosthetic valve delivery system, consistent with various embodiments of the present disclosure.

FIG. 7A illustrates a prosthetic valve delivery system 7000. Delivery system 7000 may be configured to deliver an implant prosthetic valve 6000 within a native valve, such as a native mitral valve. Prosthetic valve delivery system 7000 may include a control handle assembly 7100, a telescoping catheter assembly 7200, a delivery capsule 7300 configured to retain a prosthetic valve (e.g. valve 6000), and, optionally, a stand 7400.

Control handle assembly 7100 may include an outer sheath control handle 7120 having a steering knob 7122 configured to steer an outer sheath 7210 of the telescoping catheter assembly 7200. Control handle assembly 7100 may also include a guide catheter control handle 7140 having a steering knob 7142 configured to steer a guide catheter 7220 of the telescoping catheter assembly 7200.

Control handle assembly 7100 may also include an implant catheter control handle 7160 having a steering knob 7168 configured to steer an implant catheter 8100 of the telescoping catheter assembly 7200. Implant catheter control handle 7160 may also include a proximal capsule portion slider 7162, a distal capsule portion knob 7170, and a distal capsule portion knob lock 7172 configured to control release of the prosthetic valve 6000 from within delivery capsule 7300. Implant catheter control handle 7160 may also include a slide lock 7166 configured to lock the implant catheter control handle 7160 at a position within track 7420 of stand 7400.

Control handle assembly 7100 may also include a cradle 7180, which may be secured to stand 7400 via a locking mechanism that can be released by actuated of release button 7184. Cradle 7180 may include a rotation knob 7182 configured to control rotation of the outer sheath 7210 and guide catheter 7220. Cradle 7180 may also include a rotation knob 7186 configured to control rotation of the implant catheter 8100. Cradle 7180 may also include a knob 7188 configured to control relative axial movement between outer sheath control handle 7120 (which may be secured to outer sheath 7210) and guide catheter control handle 7140 (which may be secured to guide catheter 7220).

Figure 7B:
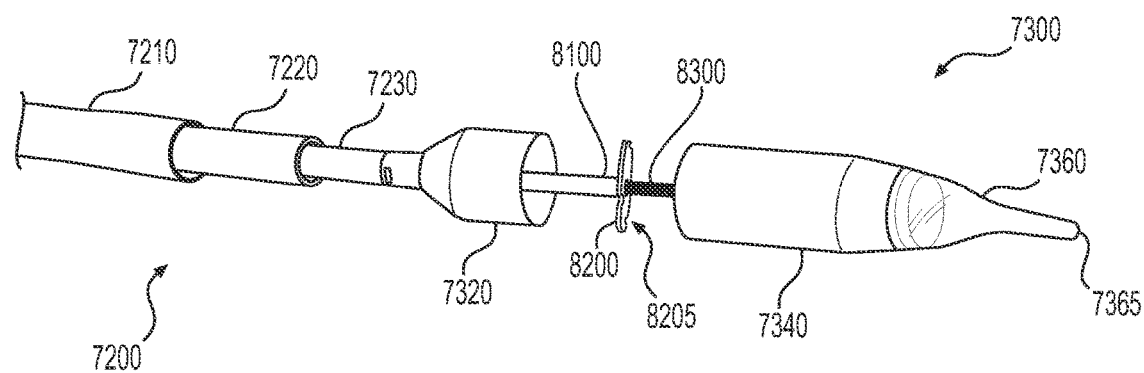
FIG. 7B illustrates an enlarged view of a delivery capsule of the exemplary prosthetic valve delivery system of FIG. 7A, consistent with various embodiments of the present disclosure.

FIG. 7B illustrates an enlarged view of delivery capsule 7300 of prosthetic valve delivery system 7000. Delivery capsule 7300 may include a proximal capsule portion 7320 and a distal capsule portion 7340 with a nose cone 7360 secured to the distal capsule portion 7340. A nose cone distal tip 7365 may form the distal end of the delivery capsule 7300. The telescoping catheter assembly 7200 may include a capsule shaft 7230 secured to, and configured to control movement of, the proximal capsule portion 7320 (e.g., due to connection 8400 between the capsule shaft 7230 and proximal capsule portion 7320, as illustrated in FIG. 8C). Implant catheter 8100 may extend within proximal capsule portion 7320 and may have a valve anchor disc 8200 connected to the distal end of the implant catheter 8100. A torque shaft 8300 may extend from the implant catheter 8100 and may be connected to distal capsule portion 7340; accordingly, torque shaft 8300 may be configured to control axial movement of the distal capsule portion 7340 relative to the implant catheter 8100 and valve anchor disc 8200. The proximal capsule portion 7320 and a distal capsule portion 7340 may be configured to retain prosthetic valve 6000, with the prosthetic valve 6000 secured against axial movement by valve anchor disc 8200. Control handle assembly 7100 may be configured to control movement of the proximal capsule portion 7320 and a distal capsule portion 7340, and thus may also control release of the prosthetic valve 6000 from within the delivery capsule 7300.

Figure 7D:
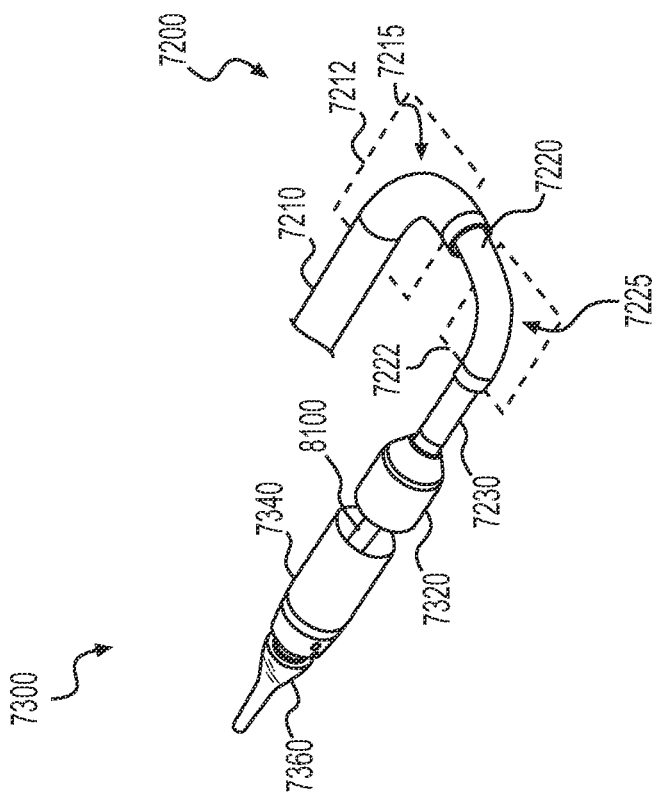
FIG. 7D illustrates another exemplary configuration of the telescoping catheter assembly and delivery capsule of FIG. 7C, consistent with various embodiments of the present disclosure.
Figure 7C:
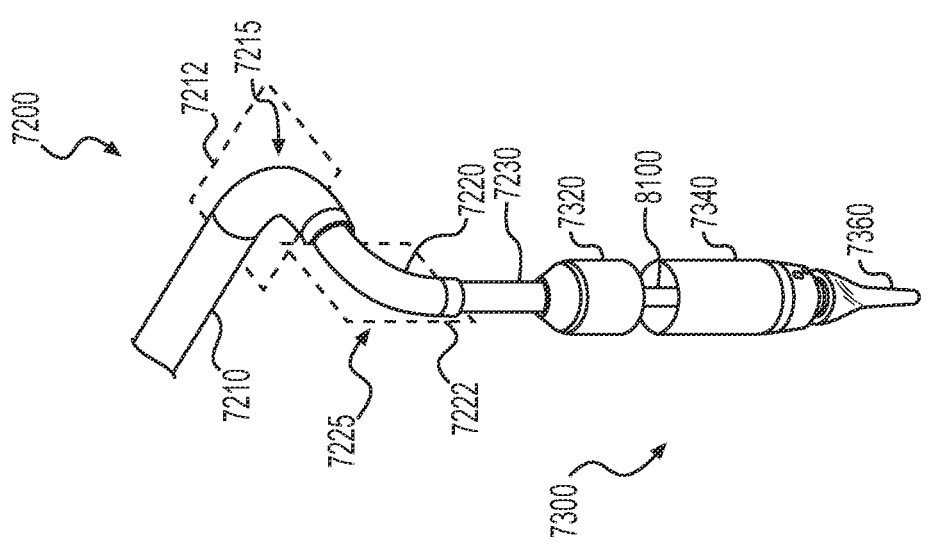
FIG. 7C illustrates an exemplary configuration of a telescoping catheter assembly and the delivery capsule of the exemplary prosthetic valve delivery system of FIG. 7A, consistent with various embodiments of the present disclosure.

FIGS. 7C and 7D illustrate exemplary configurations of the telescoping catheter assembly 7200. Outer sheath 7210 and guide catheter 7220 may include respective bending portions 7215 and 7225, at which the outer sheath 7210 and guide catheter 7220 may be configured to bend within their respective steering planes 7212 and 7222. In some embodiments, bending of the outer sheath 7210 within the first steering plane 7212 may be controlled by the outer sheath steering knob 7122 of the control handle assembly 7100. Additionally, or alternatively, bending of the guide catheter 7220 within the second steering plane 7222 may be controlled by the guide catheter steering knob 7142 of the control handle assembly 7100. In some embodiments, under control of the control handle assembly 7100, the outer sheath 7210, guide catheter 7220, and implant catheter 8100 may be steered so as to correctly position the delivery capsule 7300 within a native valve for implantation of the prosthetic valve.

Figure 8A:
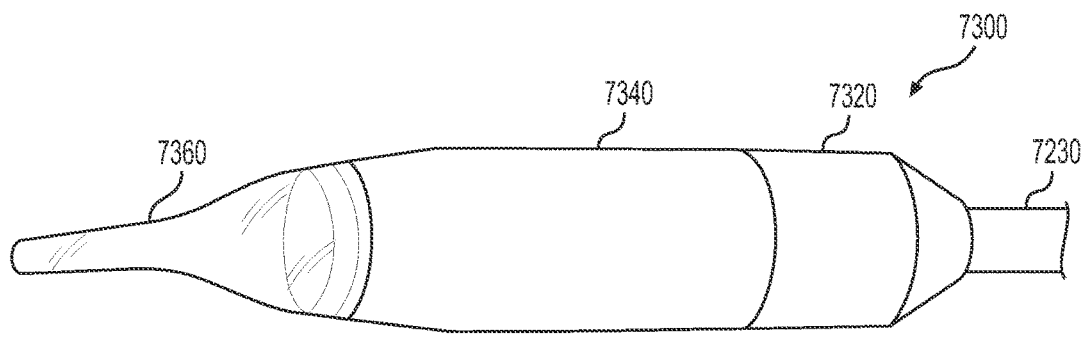
FIG. 8A illustrates another enlarged view of the exemplary delivery capsule of the prosthetic valve delivery system of FIG. 7A in a closed configuration, consistent with various embodiments of the present disclosure.
Figure 8B:
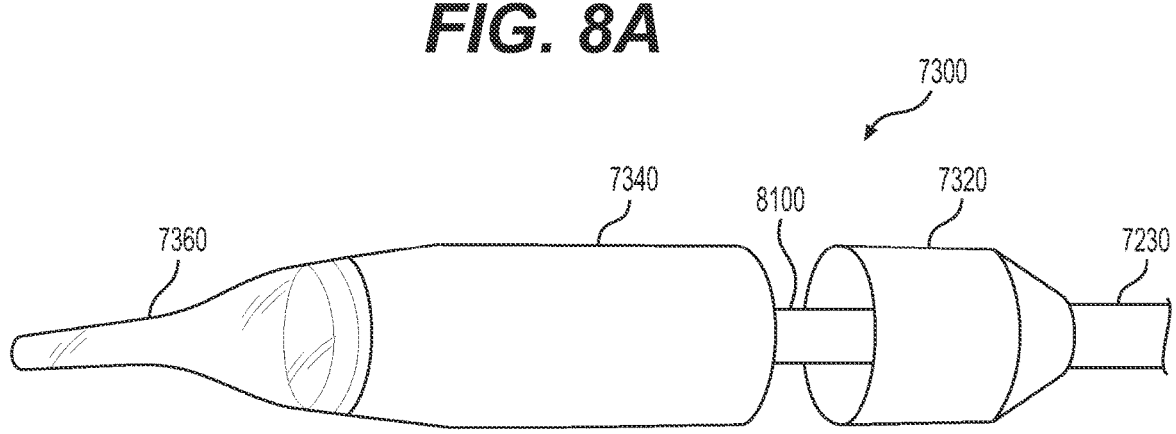
FIG. 8B illustrates the exemplary delivery capsule of FIG. 8A in an open configuration, consistent with various embodiments of the present disclosure.
Figure 8C:
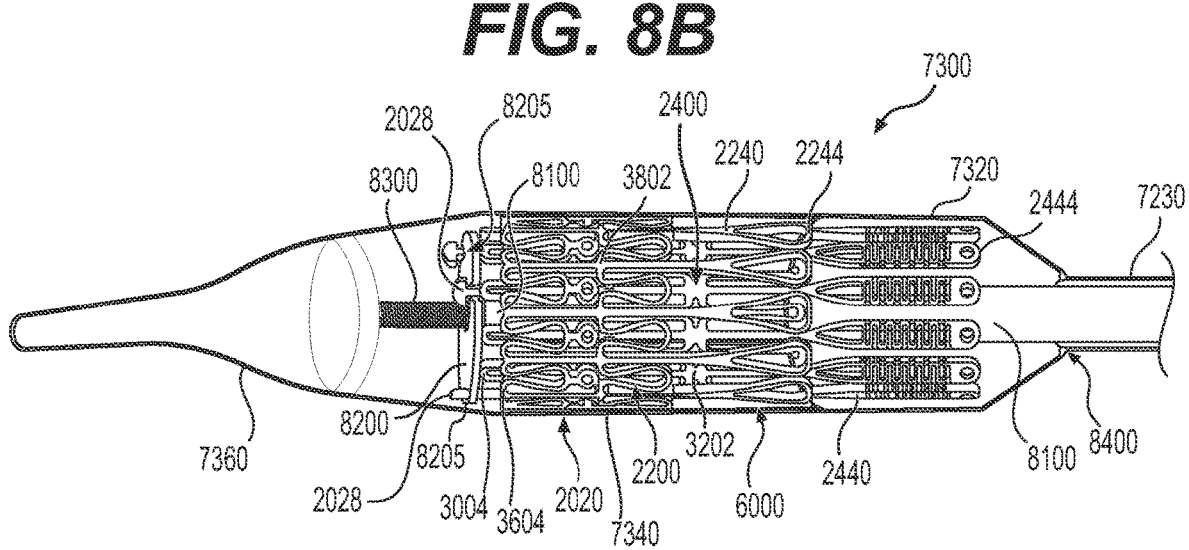
FIG. 8C illustrates an interior view of the exemplary delivery capsule of FIG. 8A in the closed configuration, consistent with various embodiments of the present disclosure.

FIG. 8A illustrates an enlarged view of delivery capsule 7300 in a closed configuration, while FIG. 8B illustrates an enlarged view of delivery capsule 7300 in an open configuration. In the closed configuration of FIG. 8A, the distal capsule portion 7340 and proximal capsule portion 7320 may be brought together to form an enclosed compartment in which prosthetic valve 6000 may be retained. In the open configuration of FIG. 8B, the distal capsule portion 7340 and proximal capsule portion 7320 may be drawn apart. In some embodiments, the delivery capsule 7300 may be configured such that the distal capsule portion 7340 and proximal capsule portion 7320 are moved apart from each other, the prosthetic valve 6000 may be sequentially deployed from within the delivery capsule and implanted within a native valve.

FIG. 8C illustrates an interior view of delivery capsule 7300 with prosthetic valve 6000 retained within the delivery capsule. Although only the valve frame 2000 of the prosthetic valve 6000 is illustrated in FIG. 8C, one of ordinary skill will understand that the entire prosthetic valve 6000 depicted in FIGS. 6A-6E may be retained within delivery capsule 7300 in the configuration illustrated in FIG. 8C.

In the embodiment illustrated in FIG. 8C, at least a portion of the annular valve body 2020 and ventricular anchoring legs 2240 of the prosthetic valve 6000 may be retained within the distal capsule portion. Additionally, or alternatively, at least a portion of atrial anchoring arms 2440 may be retained within proximal capsule portion 7320. In some embodiments, valve anchor disc 8200 may include a number of recesses 8205 configured to receive and retain the ventricular end delivery posts 2028 of the prosthetic valve 6000. For example, the valve anchor disc 8200 may include at least the same number of recesses 8205 as there are delivery posts 2028 of the prosthetic valve 6000. In some embodiments, the delivery posts 2028 may be retained within the recesses 8205 so long as the annular valve body 2020 remains in a radially-contracted configuration; the engagement between the valve anchor disc 8200 and delivery posts 2028 may secure the prosthetic valve 6000 against axial movement. Upon radial expansion of the annular valve body 2020, the delivery posts 2028 may slide or expand out of the recesses 8205, freeing the prosthetic valve 6000 from engagement with the valve anchor disc 8200.

Figure 9:
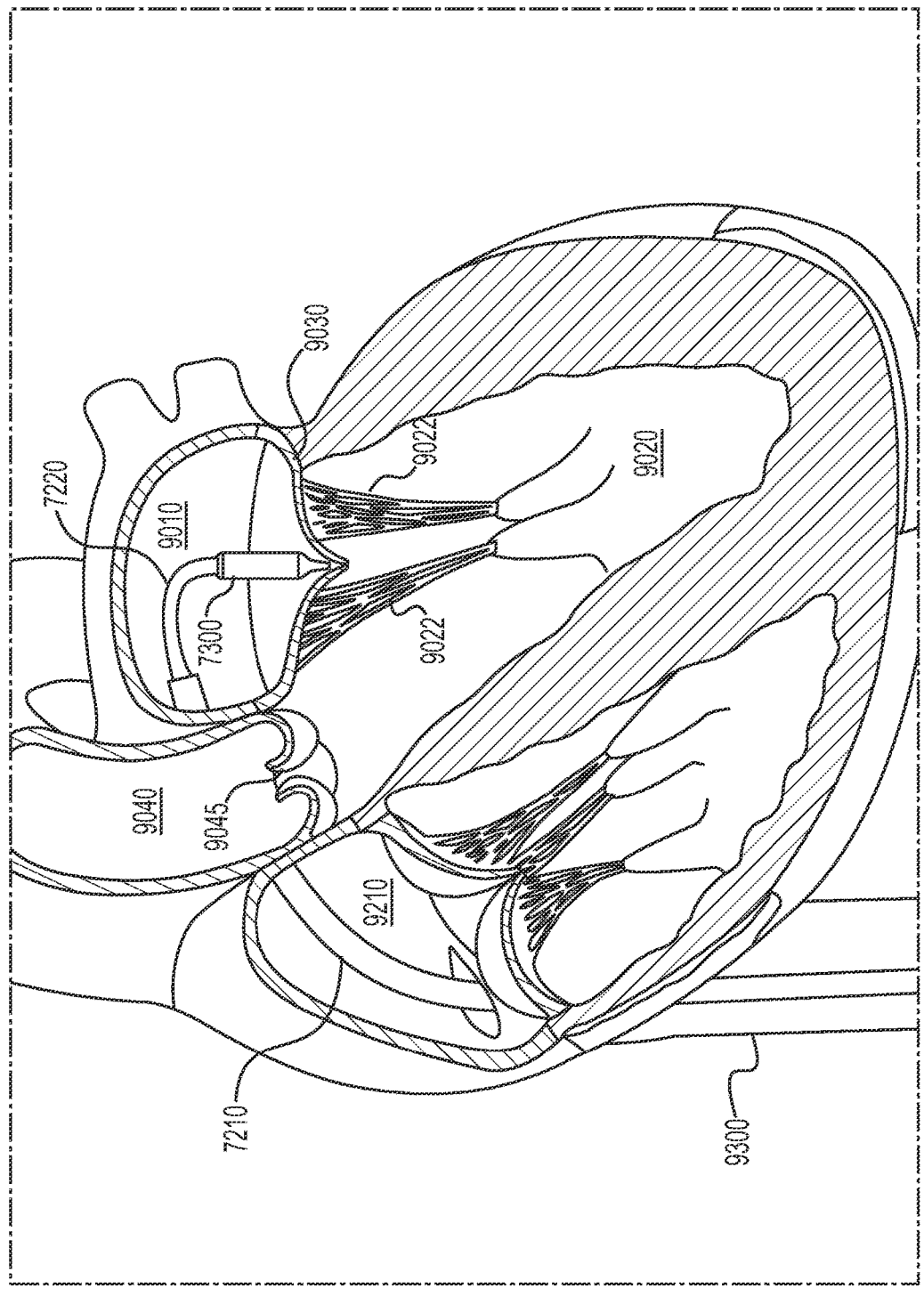
FIG. 9 illustrates advancement of the exemplary prosthetic valve delivery system of FIG. 7A into the left atrium, consistent with various embodiments of the present disclosure.

FIG. 9 illustrates one exemplary advancement route of the delivery capsule 7300 to the left atrium. In the example illustrated in FIG. 9, the delivery capsule 7300 may be steered through the vena cava into the right atrium 9210 and may pierce the interatrial septum and enter the left atrium 9010. Alternatively, the delivery capsule may be delivered to the heart by other routes. FIG. 9 also depicts the left ventricle 9020, the mitral valve 9030, the chordae tendineae 9022, the aortic valve 9045, and the aorta 9040.

Figure 10A:
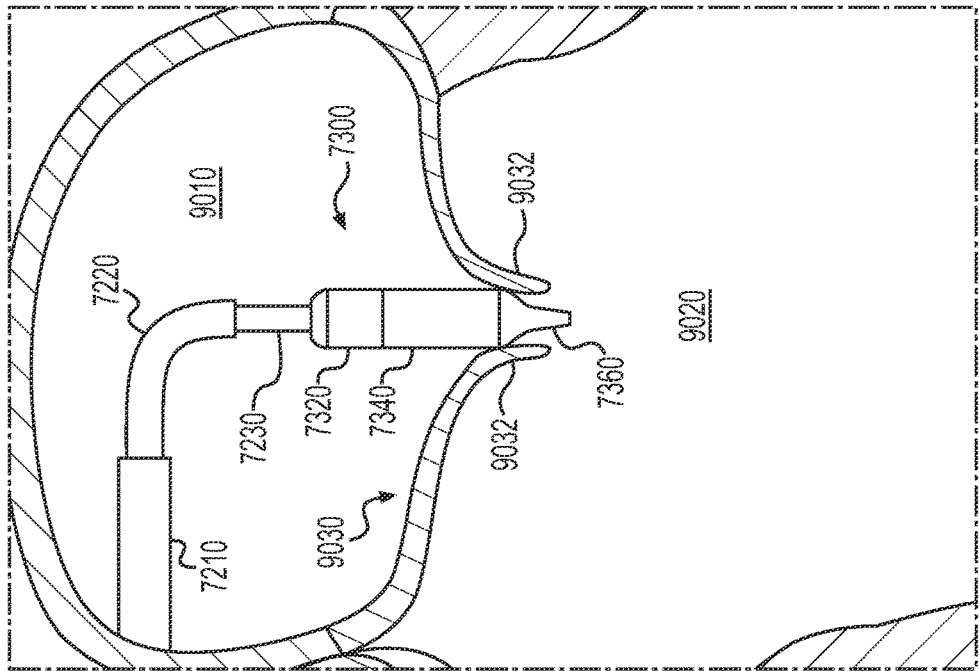
FIGS. 10A-10H depict implantation of the prosthetic valve of FIGS. 6A-6E within a native mitral valve by the exemplary prosthetic valve delivery system of FIG. 7A, consistent with various embodiments of the present disclosure.
Figure 10B:
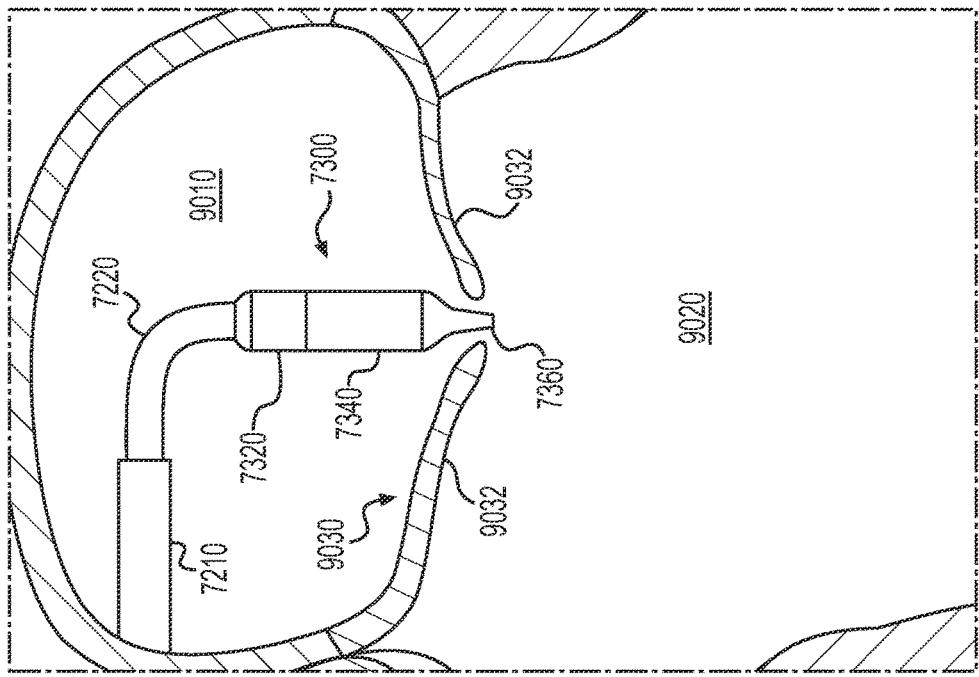
Figure 10D:
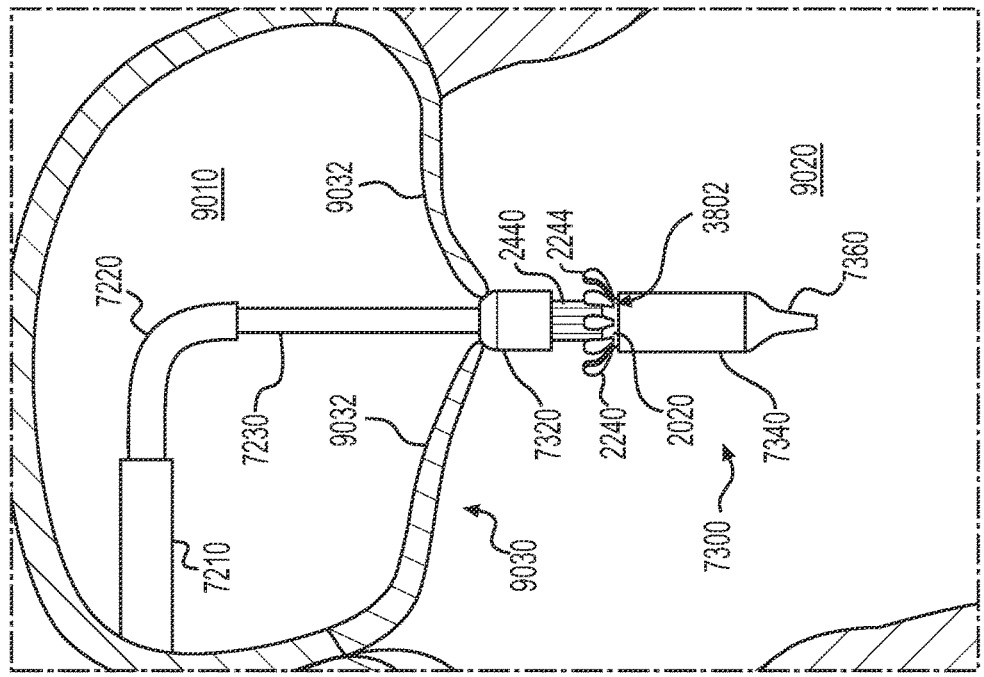
Figure 10C:
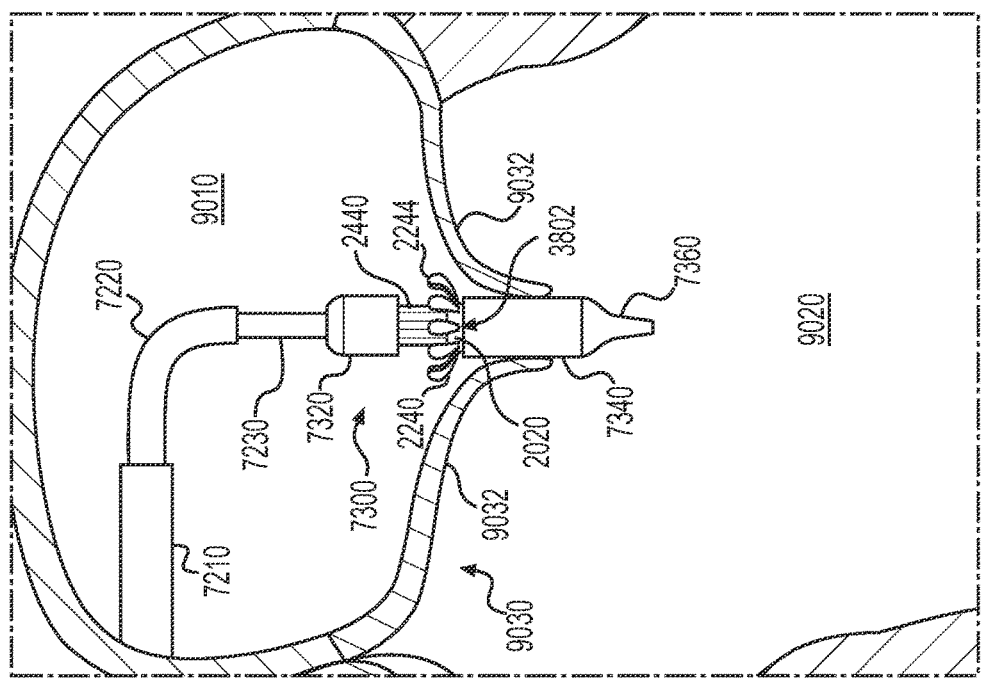

FIGS. 10A-10H depict an exemplary implantation method of prosthetic valve 6000 within a mitral valve 9030. In FIG. 10A, the delivery capsule 7300 may be coaxially aligned with the mitral valve 9030. In some embodiments, the prosthetic valve 6000 may be held within the delivery capsule 7300 while the prosthetic valve is arranged in the configuration of FIG. 5A. In FIG. 10B, the delivery capsule 7300 may be distally advanced into the mitral valve 9030. In FIG. 10C, the distal capsule portion 7340 may be distally advanced relative to the rest of the delivery capsule 7300. This may release the ventricular anchoring legs 2240 from the distal capsule portion 7340, while the atrial anchoring arms 2440 and annular valve body 2020 remain constrained within the delivery capsule. In the example shown in FIG. 10C, the ventricular anchoring legs 2240 may be released from the delivery capsule 7300 within the atrium 9010. In some embodiments, the prosthetic valve 6000 may assume the configuration of FIG. 5B when the ventricular anchoring legs 2240 are released in the step depicted in FIG. 10C.

Figure 10F:
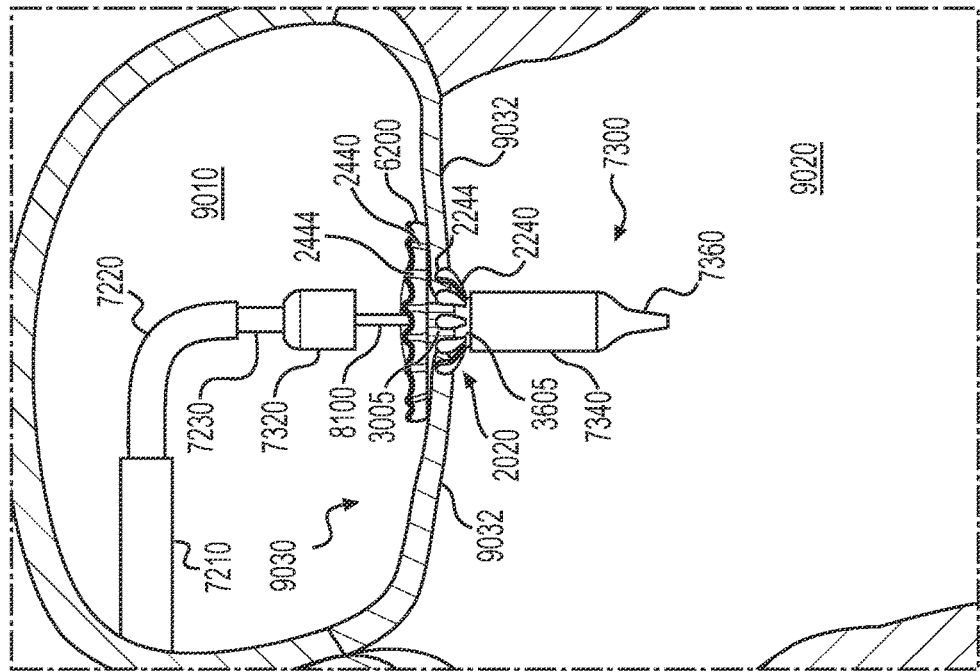
Figure 10E:
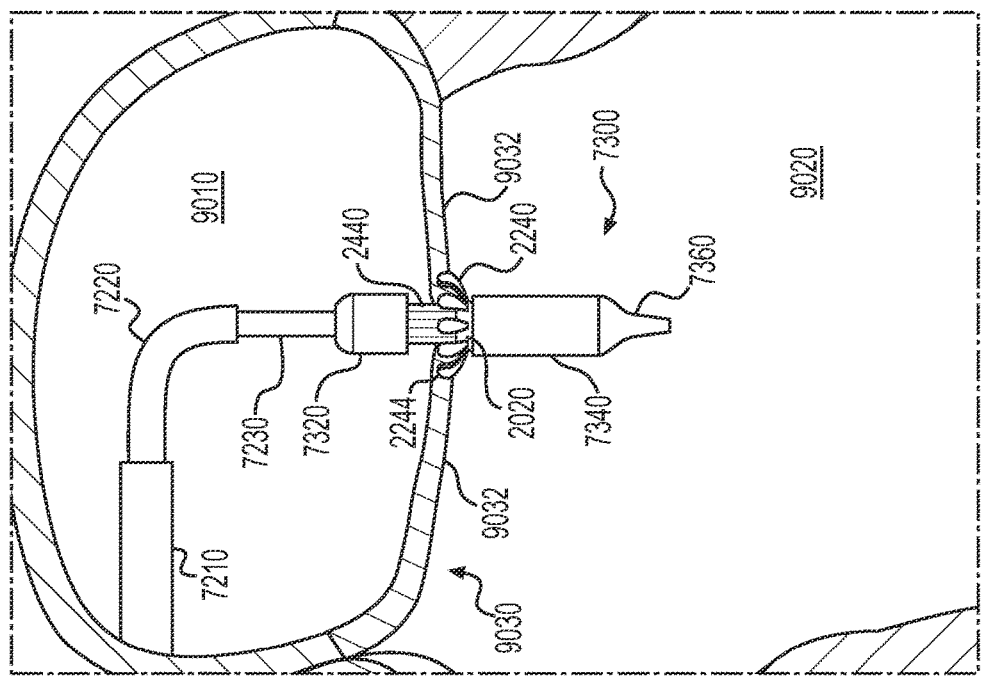

In FIG. 10D, the released ventricular anchoring legs 2240 may be passed through the mitral valve 9030 and into the left ventricle 9020. In FIG. 10E, the released legs 2240 may be proximally retracted until the ventricular anchoring legs come into contact with the ventricular tissue of the mitral valve 9030. In FIG. 10F, the proximal capsule portion 7320 may be retracted proximally, thus releasing the atrial anchoring arms 2440 within atrium 9010 while the annular valve body 2020 remains radially constrained within the distal capsule portion 7340. In some embodiments, the prosthetic valve 6000 may assume the configuration of FIG. 5D when the atrial anchoring arms 2440 are released in the step of FIG. 10F.

Figure 10H:
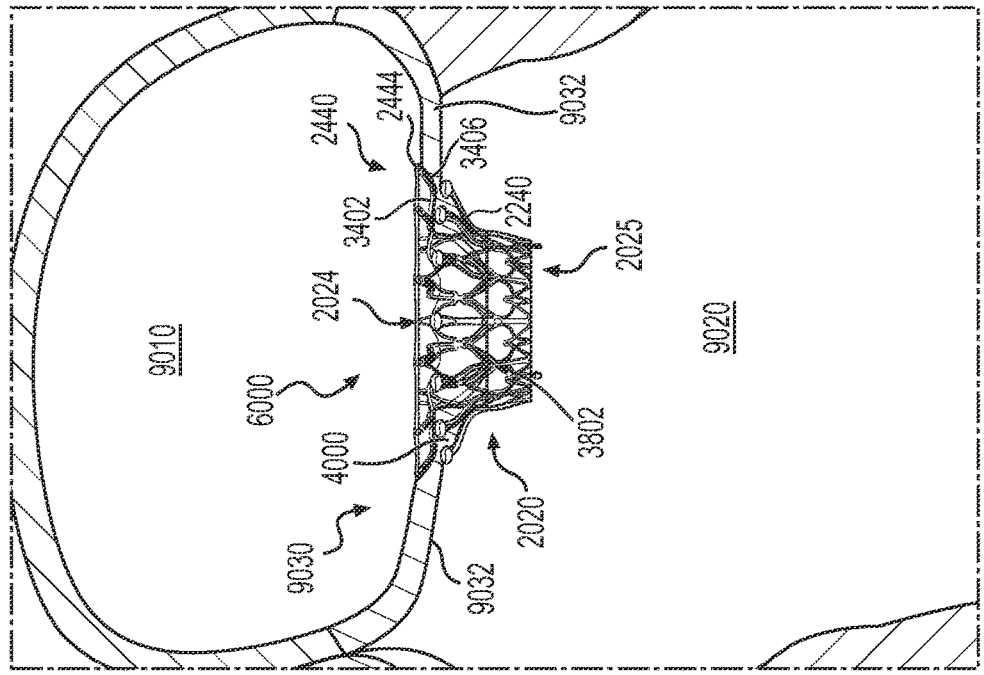
Figure 10G:
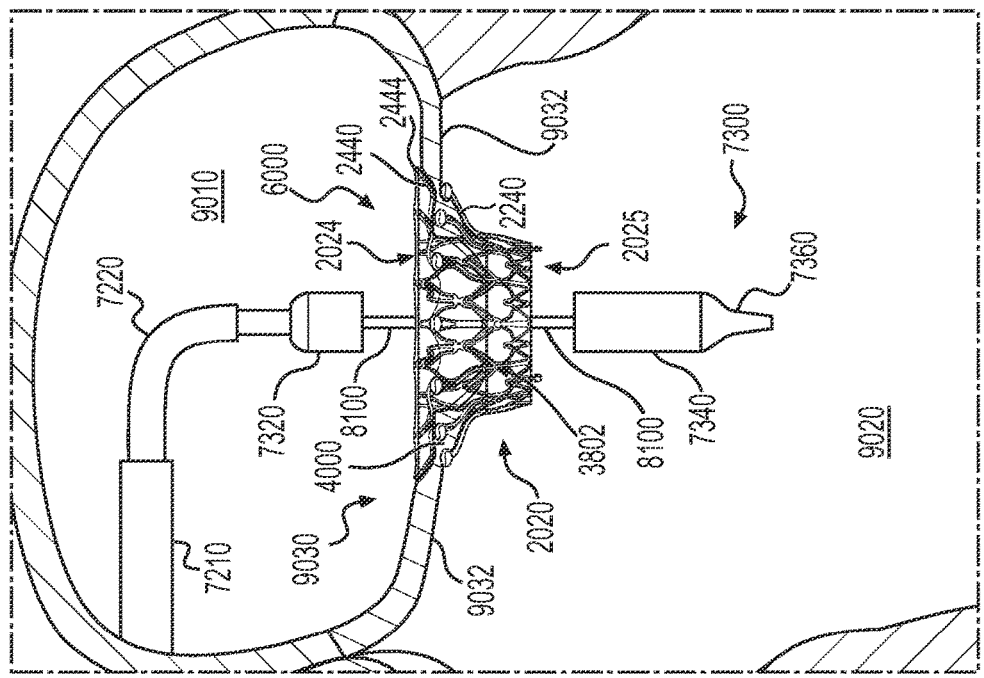

In FIG. 10G, the distal capsule portion 7340 may be advanced further until the annular valve body 2020 is released from the capsule and allowed to radially expand. Radial expansion of the annular valve body 2020 may allow the prosthetic valve to assume the fully-expanded configuration illustrated in FIG. 5E. At this stage, prosthetic valve 6000 may be securely implanted within mitral valve 9030. In FIG. 10H, the delivery system 7000, including capsule 7300, may be removed.

Various embodiments in accordance with the present disclosure relate to methods of implanting prosthetic valves within the body. While the present disclosure provides examples of methods of implanting prosthetic heart valves, and in particular methods of implanting prosthetic mitral valves, it should be noted that aspects of the disclosure in their broadest sense, are not limited to methods of implanting prosthetic heart valves. Rather, it is contemplated that aspects of the present disclosure may be applied to methods for implanting other prosthetic or implantable devices as well and are not limited to methods for implanting prosthetic valves, heart valves, or mitral valves. Prosthetic heart valve 6000, illustrated in FIGS. 6A-6E, is one example of a prosthetic valve in accordance with the present disclosure.

In some embodiments, exemplary methods may be provided for implanting a prosthetic valve at a treatment site within the body, such as within or adjacent to a native mitral valve between a heart atrium (i.e., the left atrium) and a heart ventricle (i.e., the left ventricle). In some embodiments, the exemplary method may include delivery of the prosthetic valve to the implantation site (e.g., a native mitral valve) via a variety of approaches, such as transapically, transatrially, and/or transseptally. In some embodiments, the method may include implantation of the prosthetic valve in the annulus or orifice of a native heart valve structure (e.g., a native mitral valve). For example, FIGS. 10A-10H illustrate an example of implanting a prosthetic valve 6000 within a native mitral valve 9030 between a heart atrium 9010 and a heart ventricle 9020. Exemplary methods may include firmly anchoring a prosthetic valve within the native heart valve structure, thus preventing the prosthetic valve from migrating or dislodging from within the native valve structure.

In some embodiments, exemplary methods may be provided for implanting an expandable prosthetic valve. For example, an exemplary prosthetic valve may be expandable, such as between a radially-contracted configuration (e.g., a crimped state) and a radially-expanded configuration. FIG. 5A illustrates an example of a valve frame 2000 of a prosthetic valve in a radially-contracted configuration. The diameter of the prosthetic valve may be reduced in the radially-contracted configuration. In some embodiments, the prosthetic valve may be held in the radially-contracted configuration, such as within a delivery device, during delivery of the prosthetic valve to the implantation site. Accordingly, in some embodiments, the radially-contracted configuration may also be a delivery configuration, in which the prosthetic valve is arranged for delivery to the implantation site. Once at or near the implantation site, the prosthetic valve may be radially expanded to a radially-expanded configuration, in which the prosthetic valve may be anchored at the implantation site. FIG. 5E illustrates an example of valve frame 2000 in a radially-expanded configuration. In some embodiments, the radially-expanded configuration may also be a deployed configuration, in which the prosthetic valve is released from the delivery tool and seated at the implantation site.

In some embodiments, the exemplary prosthetic valve may be configured for self-expansion to the radially-expanded configuration; that is, the prosthetic valve may be biased to assume the radially-expanded configuration due to, at least in part, the design and/or material composition of the prosthetic valve. The self-expanding prosthetic valve may be constructed of a shape memory material such as nickel titanium alloy (Nitinol), which may permit the prosthetic valve to expand to a pre-determined diameter upon removal of a constraining force and/or application of heat or energy. For example, the prosthetic valve may be contracted and held in the radially-contracted configuration by a constraining device, such as a sheath, catheter, stent, or delivery capsule. An example of such a constraining device is illustrated in FIGS. 7B and 8C, which illustrate an exemplary prosthetic heart valve 6000 held in a radially-contracted configuration within a delivery capsule 7300. When the prosthetic valve is positioned at or near the implantation site, the constraining force may be removed (e.g., valve 6000 may be removed from capsule 7300) and the prosthetic valve allowed to self-expand to the radially-expanded configuration. Additionally, or alternatively, an exemplary prosthetic valve may be configured to expand due to application of radially expansive forces thereupon. For example, the prosthetic valve may be placed, in its radially-contracted configuration, upon an expansion device such as a balloon catheter. Upon positioning at the implantation site, the expansion device may exert an outwardly-directed force upon the prosthetic valve, causing it to expand to the fully-expanded configuration.

In some embodiments, an exemplary prosthetic valve may be configured for implantation within a native atrioventricular valve and may regulate blood flow between the atrium and ventricle. For example, prosthetic heart valve 6000 illustrated in FIGS. 6A-6C may include a fluid-impervious cuff 6200 configured to extend from an inner lumen 2022 of the prosthetic valve to terminal arm ends 2444 of a plurality of atrial anchoring arms 2440. Because cuff 6200 is constructed of a fluid-impervious material, cuff 6200 may be configured to minimize or block flow of blood and other fluids through any portion of the prosthetic valve 6000 except for lumen 2022. In addition, atrial anchoring arms 2440 of the prosthetic valve (including terminal arm ends 2444) may be configured to contact and, in some embodiments, press against atrial tissue of a native heart valve. This is illustrated in FIGS. 10G-10H, which depict atrial anchoring arms 2440 of prosthetic valve 6000 arranged in contact with, and exerting a ventricularly-directed force (that is, a force directed downwards toward ventricle 9020) upon atrial tissue of native mitral valve 9030. As a result, cuff 6200 of prosthetic valve 6000 may also be configured to minimize or block passage of blood and other fluids between the prosthetic valve 6000 (including terminal arm ends 2444) and native valve tissue, a condition known as perivalvular leakage. As a result, prosthetic valve 6000 may be configured to prohibit passage of blood and other fluids between atrium 9010 and ventricle 9020, except by passage through inner lumen 2022, in which leaflets 6602, 6604, and 6606 may be situated.

In some embodiments, the prosthetic valve may include an annular valve body. The annular valve body may be configured to receive or otherwise support a flow control device, such as one or more leaflets, for regulating flow of blood or other bodily fluids through the prosthetic valve. As a result, when the prosthetic valve is implanted within a native heart valve, the flow control device may regulate fluid passage through the native heart valve, thus restoring and/or replacing the functionality of the native valve. In some embodiments, the exemplary valve body may be annular or ring-shaped and may thus have at least one opening therein. In some embodiments, the at least one opening may extend longitudinally along the entire length of the annular valve body. For example, FIG. 6D illustrates an exemplary prosthetic heart valve 6000 including an annular valve body 2020 having an axial lumen 2022 extending longitudinally therethrough. Annular valve body 2020 may receive a flow control device, such as leaflets 6602, 6604, and 6606, within lumen 2022. In some embodiments, the annular valve body may be sized and configured to be seated within the orifice of a native mitral valve. For example, as depicted in FIG. 10H, annular valve body 2020 may be situated within the orifice of mitral valve 9030, including between native leaflets 9032. In some embodiments, the annular valve body may be configured to have a smaller diameter, when fully-expanded, than the diameter of the orifice of the native mitral valve. In such embodiments, the annular valve body may be anchored in the native mitral valve by anchoring structures, such as atrial anchors and/or ventricular anchors. Alternatively, the annular valve body may be configured to expand to an equal or greater diameter than the diameter of the mitral valve orifice such that the annular valve body is anchored within the mitral valve. The annular valve body may have a circular, oval-shaped, elliptical, or D-shaped cross-section and may be symmetrical about at least one axis thereof.

In some embodiments, the prosthetic valve may additionally or alternatively include a plurality (that is, one or more) of ventricular anchors and a plurality (that is, one or more) of atrial anchors. The ventricular and atrial anchors may be configured to anchor the prosthetic valve within the native mitral valve. For example, the ventricular anchors may be configured to engage ventricular tissue of the native mitral valve and the atrial anchors may be configured to engage atrial tissue of the native mitral valve, so as to anchor the prosthetic valve within the mitral valve. In some embodiments, the ventricular anchors may be configured to be positioned at least partially within a ventricle upon implantation of the prosthetic valve, and to engage ventricular tissue of a native mitral valve. Similarly, the atrial anchors may be configured to be positioned at least partially within an atrium upon implantation of the prosthetic valve, and to engage atrial tissue of a native mitral valve. For example, FIGS. 10G and 10H illustrate an exemplary prosthetic heart valve 6000 having a plurality of atrial anchoring arms 2440 and a plurality of ventricular anchoring legs 2240. Atrial anchoring arms 2440 are situated within atrium 9010 and may engage the atrial side of native mitral valve 9030 and ventricular anchoring legs 2240 are situated within ventricle 9020 and may engage the ventricular side of native mitral valve 9030, so as to secure prosthetic heart valve 6000 within the mitral valve 9030. Accordingly, ventricular anchoring legs 2240 may be considered ventricular anchors in various embodiments. Additionally, or alternatively, atrial anchoring arms 2440 may be considered atrial anchors in various embodiments.

The prosthetic valve may include one atrial anchor and/or ventricular anchor, two atrial anchors and/or ventricular anchors, three atrial anchors and/or ventricular anchors, four atrial anchors and/or ventricular anchors, five atrial anchors and/or ventricular anchors, six atrial anchors and/or ventricular anchors, seven atrial anchors and/or ventricular anchors, eight atrial anchors and/or ventricular anchors, nine atrial anchors and/or ventricular anchors, ten atrial anchors and/or ventricular anchors, eleven atrial anchors and/or ventricular anchors, twelve atrial anchors and/or ventricular anchors, thirteen atrial anchors and/or ventricular anchors, fourteen atrial anchors and/or ventricular anchors, fifteen atrial anchors and/or ventricular anchors, sixteen atrial anchors and/or ventricular anchors, seventeen atrial anchors and/or ventricular anchors, eighteen atrial anchors and/or ventricular anchors, nineteen atrial anchors and/or ventricular anchors, twenty atrial anchors and/or ventricular anchors, or any other suitable number of atrial anchors and ventricular anchors. For example, exemplary prosthetic valve 6000 depicted in FIG. 2B may include twelve atrial anchoring arms 2440 and twelve ventricular anchoring legs 2240.

In some embodiments, the atrial and ventricular anchors may be connected to the annular valve body. For example, in FIG. 2A, atrial anchoring arms 2440 (i.e., the exemplary atrial anchors) may be connected to annular valve body 2020 at arm attachment junctions 3202 and ventricular anchoring legs 2240 (i.e., the exemplary ventricular anchors) may be connected to annular valve body 2020 at leg attachment junctions 3802. In some embodiments, the atrial anchors and/or the ventricular anchors may be physically connected to the annular valve body, such as by welding or adhesive. In some alternative embodiments, the atrial anchors and/or the ventricular anchors may be integrally formed with the annular valve body. In some embodiments, one or both of the atrial and ventricular anchors (or portions thereof) may be configured to extend radially outward from the annular valve body. For example, FIGS. 5D and 5E illustrate embodiments in which at least a portion of the atrial anchoring arms 2440 and ventricular anchoring legs 2240 extend radially outward from annular valve body 2020 (that is, extend in a direction away from the longitudinal axis of the prosthetic valve). Additionally, or alternatively, one or both of the atrial anchors and ventricular anchors may be arranged in a position in which the atrial anchors and/or ventricular anchors do not extend radially outward from the annular valve body. For example, FIG. 5A illustrates an embodiment in which atrial anchoring arms 2440 and ventricular anchoring legs 2240 do not extend radially outward from annular valve body 2020, but are instead arranged substantially parallel to the longitudinal axis of the prosthetic valve. The configuration illustrated in FIG. 5A may correspond to a radially-contracted configuration of the prosthetic valve.

In some embodiments, the locations of connection between the atrial anchors and annular valve body may be spaced at a regular interval about a circumference of the annular valve body. For example, in FIG. 2A, the atrial anchoring arms 2440 (i.e., the exemplary atrial anchors) may extend from the annular valve body 2020 at arm attachment junctions 3202. Arm attachment junctions 3202 may be spaced at a regular interval about the circumference of annular valve body 2020. Additionally, or alternatively, the locations of connection between the atrial anchors and annular valve body may be arranged along a plane perpendicular to the longitudinal axis of the prosthetic valve. For example, in FIG. 2A, the arm attachment junctions 3202 may be arranged along a plane perpendicular to longitudinal axis 2800. That is, the arm attachment junctions 3202 may be situated at the same axial position along longitudinal axis 2800.

Additionally, or alternatively, the locations of connection between the ventricular anchors and annular valve body may be spaced at a regular interval about a circumference of the annular valve body. For example, in FIG. 2A, the ventricular anchoring legs 2240 (i.e., the exemplary ventricular anchors) may extend from the annular valve body 2020 at leg attachment junctions 3802. Leg attachment junctions 3802 may be spaced at a regular interval about the circumference of annular valve body 2020. Additionally, or alternatively, the locations of connection between the ventricular anchors and annular valve body may be arranged along a plane perpendicular to the longitudinal axis of the prosthetic valve. For example, in FIG. 2A, the leg attachment junctions 3802 may be arranged along a plane perpendicular to longitudinal axis 2800. That is, the leg attachment junctions 3802 may be situated at the same axial position along longitudinal axis 2800.

In some embodiments and as illustrated in FIG. 5A, the ventricular anchoring legs 2240 (i.e., the exemplary ventricular anchors) may be retained against or substantially flush with the annular valve body 2020 when the ventricular anchoring legs are in the radially-contracted configuration. For example, in FIG. 5A, the radially-contracted ventricular anchoring legs 2240 may be held against or flush with the inner valve tubular portion 3005, which may constitute a portion of the annular valve body 2020. In some embodiments, at least a portion of the ventricular anchoring legs 2240 may contact a portion of the inner valve tubular portion 3005 when the ventricular anchoring legs are in the radially-contracted configuration.

In some embodiments, the prosthetic valve may be constrained from expansion, including radial expansion, during delivery of the prosthetic valve to an implantation site. For example, the prosthetic valve may be received at least partially within a delivery device, which may exert a radially-constraining force on the prosthetic valve, constraining the prosthetic valve against radial expansion. For example, FIG. 8C illustrates prosthetic valve 6000 received within, and radially constrained by, delivery capsule 7300. Prosthetic valve 6000 may be delivered into the heart within and deployed within the mitral valve 9030 by the delivery capsule 7300. In some alternative embodiments, the prosthetic valve may be constrained from expansion during delivery by other means, such as a sheath, catheter, or stent. In some embodiments, the exemplary prosthetic valve may be arranged in the configuration illustrated in FIG. 5A during delivery.

As illustrated in FIG. 8C, capsule 7300 may be a hollow structure, such as a vessel, container, receptacle, or the like, configured to hold the prosthetic valve 6000 at least partially therein. The capsule 7300 may include a proximal capsule portion 7320 and a distal capsule portion 7340 configured to move relative to each other so as to selectively retain and release the prosthetic valve 6000. In some embodiments, the distal capsule portion 7340 may be configured to retain at least a portion of the annular valve body 2020 and at least a portion of the ventricular anchoring legs 2240 (i.e., the exemplary ventricular anchors) therein. Distal (i.e., ventricular) movement of the distal capsule portion 7340 may release the annular valve body 2020 and ventricular anchoring legs 2240 from the distal capsule portion, thus permitting the valve body and ventricular anchors to radially expand (e.g., due to their shape memory properties). In some embodiments, the proximal capsule portion 7320 may be configured to retain at least a portion of the atrial anchoring arms 2440 (i.e., the exemplary atrial anchors) therein. Proximal (i.e., atrial) movement of the proximal capsule portion 7320 may release the atrial anchoring arms 2440 from the proximal capsule portion, thus permitting the atrial anchors to radially expand (e.g., due to their shape memory properties).

FIGS. 9 and 10A illustrate an exemplary method of delivering the prosthetic valve to the heart and into the left atrium 9010, so that the prosthetic valve may be implanted within the native mitral valve. The prosthetic valve may be retained within delivery capsule 7300 during delivery; as illustrated in FIG. 7A, delivery capsule 7300 may be situated at the distal end of exemplary prosthetic valve delivery system 7000. As illustrated in FIG. 9, delivery capsule 7300 may be transfemorally delivered into the heart, such as along a guidewire; that is, the delivery system may advance the capsule from the femoral vein and through the vena cava 9300 into the right atrium 9210. The delivery system may pass the capsule 7300 through the septum and into the left atrium 9010. In alternative embodiments, other techniques may be utilized to position capsule 7300 within the left atrium 9010, such as a transaortic approach or a transapical approach.

As illustrated in FIG. 7A, exemplary prosthetic valve delivery system 7000 may include an outer sheath 7210, guide catheter 7220, and implant catheter 8100 configured to correctly align the capsule 7300 with the native mitral valve and control advancement of the capsule through the mitral valve. In some embodiments, outer sheath 7210 and guide catheter 7220 may be steered via controlled, independent bending of both the outer sheath 7210 and guide catheter 7220, as well as controlled rotation of the outer sheath 7210 and guide catheter 7220 about their respective longitudinal axes. As a result, outer sheath 7210 and guide catheter 7220 may be bent and/or rotated to co-linearly align the capsule 7300 with the native mitral valve 9030, as illustrated in FIG. 10A. The capsule 7300 may then be distally advanced towards the mitral valve 9030 until at least a portion of the capsule is situated within the mitral valve, as illustrated in FIG. 10B. In some embodiments, distal and proximal advancement of the capsule 7300 may be controlled by implant catheter control handle 7160 of FIG. 7A. For example, implant catheter control handle 7160 may be connected to, and configured to control axial movement of, implant catheter 8100, which may in turn control advancement of the prosthetic valve and of delivery capsule 7300. Accordingly, in some embodiments, the advancement of the prosthetic valve and of delivery capsule 7300 towards the mitral valve 9030, as illustrated in FIG. 10B, may be controlled by implant catheter control handle 7160.

In some embodiments, the exemplary method for implanting an expandable prosthetic valve may include releasing the plurality of ventricular anchors within the atrium. For example, the plurality of ventricular anchors may be removed, at least in part, from a delivery device configured to radially constrain the ventricular anchors (e.g., distal capsule portion 7340). In some embodiments, the terminal ends of the ventricular anchors may deflect radially outward relative to the annular valve body when the ventricular anchors are released; this may be due, at least in part, to the shape memory properties of the ventricular anchors. In some embodiments, the entire length of the ventricular anchors may be released within the atrium; alternatively, a portion of the ventricular anchors, including the terminal ends of the ventricular anchors, may be released within the atrium. For example, FIG. 10C illustrates an embodiment in which ventricular capsule portion 7340 is advanced distally (i.e., towards ventricle 9020) until at least a portion of the ventricular anchoring legs 2240 (i.e., the exemplary ventricular anchors) are released from the distal capsule portion 7340. As a result, the terminal leg ends 2244 may deflect radially outwards, relative to the annular valve body 2020. In some embodiments, the proximal capsule portion 7320 may remain stationary during the distal advancement of the distal capsule portion 7340 to release of the ventricular anchoring legs 2240. As FIG. 10C illustrates, the ventricular anchoring legs 2240 may be released from the distal capsule portion 7340 when the ventricular anchoring legs 2240 are situated within atrium 9010. In some embodiments, the entire radial length of the ventricular anchors may be released (e.g., from distal capsule portion 7340) within the atrium. In some alternative embodiments, a portion of the ventricular anchors, including their terminal ends, may be released within the atrium. In some embodiments, the exemplary prosthetic valve may be arranged in the configuration illustrated in FIG. 5B after release of the ventricular anchors. As FIG. 5B illustrates, the terminal leg ends 2244 may deflect radially outwards while the annular valve body 2020 and, optionally, the atrial anchoring arms 2440 (i.e., the exemplary atrial anchors) remain radially constrained.

In some embodiments, the exemplary method for implanting an expandable prosthetic valve may include releasing the plurality of atrial anchors within the atrium. For example, the plurality of atrial anchors may be removed, at least in part, from a delivery device configured to radially constrain the atrial anchors (e.g., proximal capsule portion 7320). In some embodiments, the terminal ends of the atrial anchors may deflect radially outward relative to the annular valve body when the atrial anchors are released; this may be due, at least in part, to the shape memory properties of the atrial anchors. In some embodiments, the entire length of the atrial anchors may be released within the atrium; alternatively, a portion of the atrial anchors, including the terminal ends of the atrial anchors, may be released within the atrium. For example, FIG. 10F illustrates an embodiment in which proximal capsule portion 7320 is advanced proximally (i.e., towards atrium 9010) until the atrial anchoring arms 2440 (i.e., the exemplary atrial anchors) are released from the proximal capsule portion 7320. As a result, the terminal arm ends 2444 may deflect radially outwards, relative to the annular valve body 2020. As FIG. 10F illustrates, the atrial anchoring arms 2440 may be released from the proximal capsule portion 7320 when the atrial anchoring arms 2440 are situated within atrium 9010. In some embodiments, the entire radial length of the atrial anchors may be released within the atrium, as illustrated in the embodiment of FIG. 10F. In some alternative embodiments, a portion of the atrial anchors, including their terminal ends, may be released within the atrium.

In some embodiments, the ventricular anchors may be released within the atrium prior to release of the atrial anchors within the atrium. For example, the atrial anchors may remain radially-constrained with a delivery device during release of the ventricular anchors within the atrium. FIGS. 10C-10G illustrate an exemplary method in which the ventricular anchoring legs 2240 (i.e., the exemplary ventricular anchors) are released from the distal capsule portion 7340 (FIG. 10C) while the atrial anchoring arms 2440 (i.e., the exemplary atrial anchors) remain radially-constrained with the proximal capsule portion 7320. After release of the ventricular anchoring legs 2240, the atrial anchoring arms 2440 may be released from the proximal capsule portion 7320 (FIG. 10G). In some embodiments, the exemplary prosthetic valve may be arranged in the configuration illustrated in FIG. 5B prior to release of the atrial anchors, and may be arranged in the configuration illustrated in FIG. 5D after release of the atrial anchors. For example, FIG. 5D illustrated an embodiment in which atrial anchoring arms 2440 and ventricular anchoring legs 2240 have been released, thus allowing terminal arm ends 2444 and terminal leg ends 2244 to deflect radially outward. However, annular valve body 2020 may remain radially-constrained in the configuration of FIG. 5D. In some alternative embodiments, the atrial anchors may be released within the atrium prior to release of the ventricular anchors within the atrium. For example, the ventricular anchors may remain radially-constrained with a delivery device during release of the atrial anchors within the atrium. In some embodiments, the exemplary prosthetic valve may be arranged in the configuration illustrated in FIG. 5C in the event that the atrial anchors are released prior to release of the ventricular anchors. As FIG. 5C illustrates, the terminal arm ends 2444 may deflect radially outwards while the annular valve body 2020 and, optionally, the ventricular anchoring legs 2240 remain radially constrained.

In some embodiments, the exemplary method for implanting an expandable prosthetic valve may include moving the ventricular anchors, after they are released within the atrium, through the mitral valve and into the ventricle. For example, FIGS. 10C and 10D illustrate advancement of the released ventricular anchoring legs 2240 (i.e., the exemplary ventricular anchors) from the atrium 9010, where the ventricular anchoring legs 2240 were released, and through the mitral valve 9030 into the ventricle 9020. The ventricular anchoring legs 2240 and atrial anchoring arms 2440 (i.e., the exemplary atrial anchors) may remain fixed in their positions relative to the distal capsule portion 7340 and proximal capsule portion 7320, respectively, during advancement of the ventricular anchoring legs into the ventricle 9020. In some embodiments, advancement of the released ventricular anchoring legs 2240 into the ventricle 9020 may be controlled by implant catheter control handle 7160 illustrated in FIG. 7A. For example, the released ventricular anchoring legs 2240, as well as the rest of the prosthetic valve, may be secured relative to implant catheter 8100 of FIGS. 7B and 8C, which may be connected to, or otherwise secured relative to, the implant catheter control handle 7160. Accordingly, the implant catheter control handle 7160 may be utilized to control advancement of the deployed ventricular anchoring legs 2240 into the ventricle.

In some embodiments, the mitral valve tissue may be deflected by advancement of the released ventricular anchors through the mitral valve, after which the mitral valve tissue may flex back into its natural position. This is illustrated in FIGS. 10C and 10D, which depict deflection of mitral valve leaflets 9032 during passage of ventricular anchoring legs 2240 (i.e., the exemplary ventricular anchors) through the mitral valve 9030. In some embodiments, the ventricular anchors may be advanced so far into the ventricle that at least a portion of the atrial anchors may be positioned in the ventricle; alternatively, the atrial anchors may remain in the atrium.

In some embodiments, the released ventricular anchors may be moved into the ventricle prior to release of the atrial anchors within the atrium. That is, the ventricular anchors may be released in the atrium and moved into the ventricle prior to release of the atrial anchors within the atrium. For example, the atrial anchors may remain constrained within a delivery device during release of the ventricular anchors and movement of the ventricular anchors into the ventricle. This is illustrated in FIGS. 10C and 10D, which depict at least a portion of atrial anchoring arms 2440 (i.e., the exemplary atrial anchors) constrained within proximal capsule portion 7320 during release of the ventricular anchoring legs 2240 within atrium 9010 and passage of the ventricular anchoring legs into the ventricle 9020. In some embodiments, the exemplary prosthetic valve may be arranged in the configuration illustrated in FIG. 5B while the released ventricular anchors are moved into the ventricle. As FIG. 5B illustrates, the terminal leg ends 2244 may deflect radially outwards while the annular valve body 2020 and atrial anchoring arms 2440 remain radially constrained. Advantageously, movement of the ventricular anchors into the ventricle prior to release of the atrial anchors may permit the ventricular anchors to be properly positioned relative to the mitral valve prior to release of the atrial anchors. That is, by retaining the atrial anchors in their radially-constrained configuration, the atrial anchors may not hinder the placement of the ventricular anchors in the ventricle.

In some embodiments, the exemplary method for implanting an expandable prosthetic valve may include releasing the annular valve body after moving the released ventricular anchors from the atrium to the ventricle. As a result of releasing the annular valve body, the prosthetic valve may be anchored within the mitral valve. In some embodiments, release of the annular valve body may also occur after releasing the ventricular anchors and atrial anchors within the atrium. For example, the annular valve body may remain radially-constrained within a delivery device during release of the atrial and ventricular anchors and during movement of the released ventricular anchors from the atrium into the ventricle, after which the annular valve body may be released from the delivery device. FIG. 10G illustrates an embodiment in which annular valve body 2020 is released from distal capsule portion 7340 after the ventricular anchoring legs 2240 (i.e., the exemplary ventricular anchors) are released from the distal capsule portion 7340 (FIG. 10C), after the released ventricular anchoring legs 2240 are moved into the ventricle 9020 (FIG. 10D), and after the atrial anchoring arms 2440 (i.e., the exemplary atrial anchors) are released from the proximal capsule portion 7320 (FIG. 10F). In the embodiment shown in FIG. 10G, the annular valve body may be released when the annular valve body is positioned in the ventricle. In other embodiments, the annular valve body may be released in a different portion of the heart. In some embodiments, the exemplary prosthetic valve may be arranged in the configuration illustrated in FIG. 5E after release of the annular valve body. As FIG. 5E illustrates, annular valve body 2020, atrial anchoring arms 2440, and ventricular anchoring legs 2240 may be fully deployed upon release of the annular valve body. In some embodiments, the annular valve body may radially expand when released, thus anchoring the prosthetic valve within the mitral valve.

In some embodiments, the annular valve body, atrial anchors, and ventricular anchors may be arranged within a delivery device according to the configuration illustrated in FIG. 8C. As shown in FIG. 8C, at least a portion of each atrial anchoring arm 2440 (i.e., the exemplary atrial anchors) may be retained within the proximal capsule portion 7320, including the distal arm ends 2444. The proximal capsule portion 7320 may be configured for proximal movement relative to the atrial anchoring arms 2440 (i.e., the exemplary atrial anchors); upon movement of the proximal capsule portion 7320 to a position in which the atrial anchoring arms 2440 are no longer retained therein, the atrial anchoring arms may deflect radially outwards (as illustrated in FIG. 10F).

Additionally, or alternatively, the annular valve body 2020 and ventricular anchoring legs 2240 illustrated in FIG. 8C may be retained within the distal capsule portion 7340 in such a fashion that the terminal leg ends 2244 may be situated in closer proximity to the open, proximal end of the distal capsule portion (that is, the right side of distal capsule portion 7340 in FIG. 8C) than is the annular valve body. The distal capsule portion 7340 may be configured for longitudinal movement relative to the ventricular anchoring legs 2240 (i.e., the exemplary ventricular anchors) and annular valve body 2020. In some embodiments, the distal capsule portion 7340 may be configured to advance distally until it reaches a position in which the terminal leg ends 2244 are no longer retained within the distal capsule portion 7340. As the ventricular anchoring legs 2240 emerge from the distal capsule portion 7340, they may be free from radially-constraining forces and may deflect radially outward (e.g., due to their shape-memory properties). The distal capsule portion 7340 may be moved distally until at least a portion of the ventricular anchoring legs 2240 are no longer contained within the distal capsule portion 7340, allowing the ventricular anchoring legs to deflect radially outwards (as illustrated in FIG. 10C). However, at least a portion of the annular valve body 2020 remains retained within the distal capsule portion 7340 at this longitudinal position of the distal capsule portion. Accordingly, the annular valve body 2020 remains radially-constrained by the distal capsule portion 7340 and may be prevented from radially expanding. The distal capsule portion 7340 may then be further moved in the distal direction until the annular valve body 2020 is no longer contained within the distal capsule portion. At such a point, the annular valve body 2020 may be free from radially-constraining forces and may expand radially outward due to its shape-memory properties (as illustrated in FIG. 10H).

In some embodiments, the annular valve body may be constrained from expansion (including radial expansion) during release of the ventricular anchors and atrial anchors and during movement of the ventricular anchors into the ventricle. For example, as illustrated in FIGS. 10C-10H, the annular valve body 2020 may remain constrained within the distal capsule portion 7340 during distal movement of the distal capsule portion 7340 to release the ventricular anchoring legs 2240 (i.e., the exemplary ventricular anchors) (FIG. 10C), during passage of the released ventricular anchoring legs 2240 into the ventricle 9020 (FIG. 10D), and during proximal movement of the proximal capsule portion 7320 to release the atrial anchoring arms 2440 (i.e., the exemplary atrial anchors) (FIG. 10F). For example, after movement of the distal capsule portion 7340 to the position at which the ventricular anchoring legs 2240 are released, further movement of the distal capsule portion may be prevented until release of the annular valve body 2020 is desired. In some embodiments, constraining the annular valve body against expansion may permit the atrial anchors and ventricular anchors to be positioned at their desired locations, such as within the atrium and ventricle, respectively. Upon expansion of the annular valve body, the prosthetic valve may be secured within the mitral valve.

After release of the atrial anchors and ventricular anchors, but prior to release of the annular valve body (i.e., the configuration of FIG. 10F), the prosthetic valve may be configured to assume a configuration similar to the configuration of the prosthetic valve illustrated in FIG. 5D. FIG. 5D illustrates a configuration in which atrial anchoring arms 2440 and ventricular anchoring legs 2240 have been released, but annular valve body 2020 remains radially constrained. In the configuration of FIG. 5D, the terminal leg ends 2244 may be spaced apart from the atrial anchoring arms 2440 (in particular, from arm portions 3504 and 3506) by distance 5004. Due to the presence of the space represented by distance 5004 between the atrial anchoring arms 2440 and ventricular anchoring legs 2240, mitral valve tissue may be retained between the atrial anchoring arms 2440 and ventricular anchoring legs. However, because the atrial anchoring arms and ventricular anchoring legs do not clamp on tissue when the prosthetic valve is in this configuration, the prosthetic valve may be configured for small axial and lateral movements relative to the mitral valve tissue. As a result, the prosthetic valve may be maneuvered into the desired position with respect to the mitral valve tissue, with the native valve tissue arranged at the desired position between the atrial anchoring arms 2440 and legs 2240.

Upon release of the annular valve body, the annular valve body may radially expand due to the lack of radially-constraining forces on the annular valve body. Upon release of the annular valve body, the prosthetic valve may assume the configuration illustrated in FIGS. 10G and 10H, in which the prosthetic valve 6000 is securely anchored within mitral valve 9030; the configuration of the prosthetic valve in FIGS. 10G and 10H may be similar to the configuration of the prosthetic valve illustrated in FIG. 5E. In some embodiments, and as illustrated in FIG. 5E, the axial distance 5004 between the released atrial anchors and the released ventricular anchors may be reduced or eliminated upon release of the annular valve body. For example, in FIG. 5E, the axial distance between terminal leg ends 2244 and portions 3504 and 3506 of atrial anchoring arms 2440 (i.e., the exemplary atrial anchors) may be reduced or, in some embodiments, completely removed, relative to their respective positions in FIG. 5D. As a result, the atrial anchors and ventricular anchors may be configured to grasp or clamp tissue of the native mitral valve to securely anchor the prosthetic valve in place. For example, in the configuration illustrated in FIGS. 10G and 10H, atrial anchoring arms 2440 may exert a ventricularly-directed force (that is, a force directed downwards towards ventricle 9020 in FIGS. 10G and 10H) on the mitral valve tissue. Similarly, ventricular anchoring legs 2240 (i.e., the exemplary ventricular anchors) may exert an atrially-directed force (that is, a force directed upwards towards atrium 9010 in FIGS. 10G and 10H) on the mitral valve tissue. These opposing forces may clamp or "sandwich" the mitral valve tissue between the atrial anchoring arms 2440 and ventricular anchoring legs 2240. In some embodiments, reduction of the axial distance between the atrial anchoring arms 2440 and ventricular anchoring legs 2240 may reduce the volume between the atrial anchoring arms and ventricular anchoring legs in which mitral valve tissue is retained. This reduction in volume may cause the tissue to slightly deform the atrial anchoring arms 2440 and ventricular anchoring legs 2240. Due to their shape memory characteristics, the atrial anchoring arms 2440 and ventricular anchoring legs 2240 may resist the deformation and exert a strengthened clamping force on the mitral valve tissue between the atrial anchoring arms and ventricular anchoring legs. This clamping or "sandwiching" effect may firmly anchor prosthetic valve 6000 within mitral valve 9030. Accordingly, in some embodiments, release of the annular valve body may cause the ventricular anchors and atrial anchors to clamp native valve tissue therebetween.

Additionally, or alternatively, the ventricular anchors and the atrial anchors may shift radially outward when the annular valve body is released. That is, the ventricular anchors and atrial anchors may be positioned in closer proximity to the longitudinal axis of the prosthetic valve prior to release of the annular valve body than after release of the annular valve body. This may be due, at least in part, to the fact that the ventricular anchors and atrial anchors are secured to the annular valve body in some embodiments. Thus, release and radial expansion of the annular valve body may cause the ventricular anchors and the atrial anchors to shift radially outward. For example, FIG. 5D illustrates an embodiment of a valve frame 2000 of an exemplary prosthetic valve prior to expansion of the annular valve body 2020, and FIG. 5E illustrates an embodiment of the valve frame 2000 after expansion of the annular valve body 2020. As FIGS. 5D and 5E illustrate, the entire length of atrial anchoring arms 2440 (i.e., the exemplary atrial anchors) and ventricular anchoring legs 2240 (i.e., the exemplary ventricular anchors) may shift radially outward upon expansion of annular valve body 2020. For example, terminal arm ends 2444 and terminal leg ends 2244 may shift radially outward upon expansion of annular valve body 2020. Additionally, or alternatively, proximal arm ends 3020 and proximal leg ends 3622 may shift radially outward upon expansion of annular valve body 2020.

In some embodiments, each ventricular anchor may include a connection point to the annular valve body. The connection point may be a weld, an adhesion, an over-mold, or a continuous integration of the ventricular anchor to or with the annular valve body. Accordingly, the number of ventricular anchors of the prosthetic valve may equal the number of connection points. In FIGS. 2A, 5D, and 5E, ventricular anchoring legs 2240 may be connected to annular valve body 2020 at leg attachment junctions 3802; accordingly, in some embodiments the leg attachment junctions 3802 may constitute the connection points of the ventricular anchors to the annular valve body.

In some embodiments, the connection points of the ventricular anchors may be configured to form a first diameter during movement of the ventricular anchors into the ventricle. That is, after release of the ventricular anchors in the atrium and prior to release of the annular valve body, the connection points may be positioned around a circumference of the annular valve body in a substantially circular arrangement having a first diameter. For example, in FIGS. 5B and 5D, leg attachment junctions 3802 (i.e., the exemplary connection points of the ventricular anchors) may be arranged in a substantially circular arrangement having a diameter equal to the first diameter. In some embodiments, the first diameter may be equal to the diameter formed by the connection points of the ventricular anchors prior to release of the ventricular anchors. Alternatively, the first diameter may be larger than or smaller than the diameter formed by the connection points of the ventricular anchors prior to release of the ventricular anchors. FIGS. 10C and 10D illustrate an example in which the released ventricular anchoring legs 2240 (i.e., the exemplary ventricular anchors) are moved into the ventricle 9020 while the leg attachment junctions 3802 (i.e., the exemplary connection points of the ventricular anchors) form the first diameter.

In some embodiments, the connection points of the ventricular anchors may be configured to form a second diameter after release of the annular valve body. The second diameter of the connection points of the ventricular anchors may be larger than the first diameter of the connection points of the ventricular anchors. For example, after release of the annular valve body, the connection points may be positioned around a circumference of the annular valve body in a substantially circular arrangement having a second diameter that is larger than the first diameter. For example, in FIG. 5E, leg attachment junctions 3802 (i.e., the exemplary connection points of the ventricular anchors) may be arranged in a substantially circular arrangement having a diameter equal to the second diameter. As illustrated by FIGS. 5D and 5E, the second diameter of leg attachment junctions 3802 (shown in FIG. 5E) is larger than the first diameter of the leg attachment junctions 3802 (shown in FIG. 5D). FIGS. 10G and 10H illustrate an example in which the annular valve body 2020 has been released. Accordingly, in FIGS. 10G and 10H, the leg attachment junctions 3802 (i.e., the exemplary connection points of the ventricular anchors) form the second diameter.

In some embodiments, the exemplary method for implanting an expandable prosthetic valve may include prior to release of the annular valve body, moving the released ventricular anchors in an atrial direction such that the ventricular anchors engage tissue of the native mitral valve. This may occur, for example, after the ventricular anchors are released in the atrium and moved into the ventricle. Once the released ventricular anchors are in the ventricle, the ventricular anchors may be moved in an atrial direction to a position at which the ventricular anchors engage ventricular tissue of the native mitral valve. An example of this movement is illustrated in FIGS. 10D and 10E. In FIG. 10D, the released ventricular anchoring legs 2240 (i.e., the exemplary ventricular anchors) are moved into ventricle 9020. In FIG. 10E, the released ventricular anchoring legs 2240 are then moved in an atrial direction (that is, towards atrium 9010) until legs 2240 engage the ventricular-side tissue of mitral valve 9030. In some embodiments, movement of the released ventricular anchors in an atrial direction may occur prior to release of the annular valve body and prior to release of the atrial anchors. In the example illustrated in FIGS. 10D and 10E, atrial anchoring arms 2440 (i.e., the exemplary atrial anchors) may remain constrained within proximal capsule portion 7320 and annular valve body 2020 may remain constrained within distal capsule portion 7340 during movement of the released ventricular anchoring legs 2240 into the ventricle 9020 and the subsequent movement of the ventricular anchoring legs in the atrial direction.

In some embodiments, the ventricular anchors may be configured to pull distinct portions of the native mitral valve together. For example, the ventricular anchors may be configured to pull distinct portions of the native mitral valve together when the released ventricular anchors are positioned in the ventricle and moved in an atrial direction to engage tissue of the mitral valve. In some embodiments, the expression "distinct portions of the native mitral valve" may refer to portions of the mitral valve situated apart from each other or configured for movement relative to each other. For example, "distinct portions of the native mitral valve" may refer to the leaflets of the native mitral valve, which may be configured to move apart from and towards each other to form open and closed positions of the mitral valve. In some embodiments, the deployed ventricular anchors may be configured to firmly grasp the mitral valve leaflets and pull the leaflets together, due in part to the shape memory properties of the ventricular anchors. In some embodiments, the ventricular anchors may be configured to pull the mitral valve leaflets together until the leaflets are positioned against the radially-constrained atrial anchors and annular valve body, thus grasping and pulling the native mitral valve substantially closed. For example, as depicted in FIG. 10E, the ventricular anchoring legs 2240 are radially extended and grasp the mitral valve leaflets 9032, pulling the leaflets together until the leaflets are held against the constrained atrial anchoring arms 2440 (i.e., the exemplary atrial anchors) and annular valve body 2020. As a result, mitral valve 9030 may be held in a closed position by the deployed ventricular anchoring legs 2240.

After the released ventricular anchors are moved atrially to engage the ventricular side of the mitral valve, the atrial anchors may then be released, thus retaining the tissue between the atrial anchors and ventricular anchors. For example, as depicted in FIG. 10F, after the atrial anchoring arms 2440 are released, the mitral valve tissue may be held between the atrial anchoring arms 2440 and the ventricular anchoring legs 2240 (i.e., the exemplary ventricular anchors). Upon radial expansion of the annular valve body, illustrated in FIG. 10G, the annular anchors and ventricular anchors may grasp or "sandwich" the tissue, thus anchoring the prosthetic valve in the mitral valve.

In some alternative embodiments of the present disclosure, a method of implanting an expandable prosthetic valve within a native mitral valve between an atrium and a ventricle may be provided. In some embodiments, the exemplary method of implanting an expandable prosthetic valve may include outwardly moving terminal ends of ventricular anchors relative to a portion of an annular valve body positioned within the atrium. For example, the ventricular anchors and annular valve body may be radially-constrained within the atrium, such as within a delivery device. At least a portion of the ventricular anchors may be released from the delivery device, such that the terminal ends of the ventricular anchors may deflect radially outwards. However, the annular valve body may remain radially-constrained within the delivery device; accordingly, the terminal ends of the ventricular anchors may move outwardly relative to the constrained annular valve body. In some embodiments, the terminal ends of the ventricular anchors may be configured to move outwardly relative to a portion of the constrained annular valve body positioned within an atrium. For example, FIG. 10C illustrates an embodiment in which distal movement of the distal capsule portion 7340 releases the ventricular anchoring legs 2240 (i.e., the exemplary ventricular anchors). As a result, the terminal leg ends 2244 move radially outward relative to the annular valve body 2020, while the annular valve body 2020 remains constrained within the distal capsule portion 7340. As illustrated in FIG. 10C, at least a portion of the annular valve body 2020 may be positioned within the atrium 9010.

In some embodiments, the exemplary method of implanting an expandable prosthetic valve may include advancing at least a portion of the expandable prosthetic valve containing the ventricular anchors through the native mitral valve into the ventricle after outwardly moving the terminal ends of the ventricular anchors. In some embodiments, the atrial anchors and annular valve body may remain constrained (e.g., within delivery capsule 7300) during movement of the portion of the prosthetic valve containing the ventricular anchors into the ventricle. In some embodiments, the entire prosthetic valve, including the ventricular anchors, may be advanced into the ventricle. Alternatively, at least a portion of the prosthetic valve, including the ventricular anchors, may be advanced into the ventricle while at least another portion of the prosthetic valve remains in the atrium and/or within the orifice of the mitral valve. For example, at least a portion of the atrial anchors may remain in the atrium and/or within the orifice of the mitral valve when the portion of the prosthetic valve containing the ventricular anchors is advanced into the ventricle. For example, FIG. 10D illustrates an embodiment in which at least a portion of the prosthetic valve, including the deployed ventricular anchoring legs 2240 (i.e., the exemplary ventricular anchors), is advanced through the mitral valve 9030 and into the ventricle 9020. In the example illustrated in FIG. 10D, annular valve body 2020 and atrial anchoring arms 2440 (i.e., the exemplary atrial anchors) may remain constrained within distal capsule portion 7340 and proximal capsule portion 7320, respectively.

In some embodiments, the exemplary method of implanting an expandable prosthetic valve may include outwardly moving terminal ends of atrial anchors relative to a portion of the annular valve body while the atrial anchors are at least partially positioned within the atrium. For example, the atrial anchors may be released from a delivery device while the atrial anchors are at least partially positioned within the atrium. As a result, the terminal ends of the atrial anchors may deflect radially outwards. However, the annular valve body may remain radially-constrained within the delivery device; accordingly, the terminal ends of the atrial anchors may move outwardly relative to the constrained annular valve body. In some embodiments, the terminal ends of the atrial anchors may be moved outwardly after the terminal ends of the ventricular anchors are moved outwardly. In some embodiments, the terminal ends of the atrial anchors may be moved outwardly after the portion of the expandable prosthetic valve containing the deployed ventricular anchors is advanced through the mitral valve into the ventricle. For example, FIG. 10F illustrates an embodiment in which proximal movement of the proximal capsule portion 7320 releases the atrial anchoring arms 2440 (i.e., the exemplary atrial anchors). As a result, the terminal arm ends 2444 may move radially outward relative to the annular valve body 2020, which remains constrained within the distal capsule portion 7340. As illustrated in FIG. 10F, at least a portion of the atrial anchoring arms 2440 may be positioned within the atrium 9010 during outward movement of the terminal arm ends 2444.

In some embodiments, the exemplary method of implanting an expandable prosthetic valve may include radially expanding the annular valve body after outwardly moving the terminal ends of the ventricular anchors and outwardly moving the terminal ends of the atrial anchors. Radial expansion of the annular valve body may anchor native heart valve tissue between the atrial anchors and ventricular anchors. For example, the annular valve body may be removed from the delivery device, such that it may be free of radially-constraining forces. As a result of its shape memory properties, the annular valve body may expand radially outward, which may anchor the prosthetic valve in the mitral valve. In some embodiments, the annular valve body may be expanded within the ventricle. For example, FIG. 10G illustrates an embodiment in which distal movement of the distal capsule portion 7340 releases the annular valve body 2020 within ventricle 9020. As a result, the annular valve body 2020 may radially expand, causing the ventricular anchoring legs 2240 (i.e., the exemplary ventricular anchors) and atrial anchoring arms 2440 to firmly clamp the native valve tissue, thus anchoring prosthetic valve 6000 within mitral valve 9030. As a result, in some embodiments, expansion of the annular valve body may anchor the prosthetic valve within the native mitral valve.

In some embodiments, the ventricular anchors and the atrial anchors may be biased to assume expanded configurations and may be constrained in non-expanded configurations. For example, the ventricular anchors and atrial anchors may be biased to assume expanded configurations due to their shape memory properties. In some embodiments, the ventricular anchors and atrial anchors may be constrained by a delivery device (e.g., delivery capsule) which may be configured to exert a radially-constraining force on the ventricular anchors and atrial anchors. As a result, the ventricular anchors and atrial anchors may be constrained in a non-expanded configuration and may be prevented from deflecting radially outward. For example, FIG. 8C illustrates an embodiment in which atrial anchoring arms 2440 (i.e., the exemplary atrial anchors) and ventricular anchoring legs 2240 are constrained in non-expanded configurations by proximal capsule portion 7320 and distal capsule portion 7340, respectively, of delivery capsule 7300. In some embodiments, delivery capsule 7300 may be configured to retain the prosthetic valve in the prosthetic valve configuration illustrated in FIG. 5A.

In some embodiments, outwardly moving the respective terminal ends of the ventricular anchors and the atrial anchors may include respectively releasing constraints on the ventricular anchors and the atrial anchors. Releasing the constraints on the ventricular anchors and atrial anchors may enable the ventricular anchors and the atrial anchors to spring outwardly. For example, the ventricular anchors and atrial anchors may be released from the delivery device, thus freeing the ventricular anchors and atrial anchors from the radially-constraining forces exerted by the delivery device. As a result of the shape memory properties of the ventricular anchors and atrial anchors, the terminal ends of the ventricular anchors and atrial anchors may be configured to deflect radially outward, relative to the annular valve body. For example, releasing constraints on the ventricular anchors and atrial anchors may permit the prosthetic valve to transition from the configuration illustrated in FIG. 5A to the configuration illustrated in FIG. 5D. In the example depicted in FIG. 5D, the atrial anchoring arms 2440 and ventricular anchoring legs 2240 (i.e., the exemplary ventricular anchors) may be free from radially-constraining force; accordingly, the terminal arm ends 2444 and terminal leg ends 2244 may deflect radially outwards from the annular valve body 2020. However, the annular valve body 2020 may remain radially-constrained, such as within distal capsule portion 7340.

In some embodiments, expanding the annular valve body may include releasing the annular valve body from a constraint. As a result, the annular valve body may be enabled to expand to a pre-contraction expanded configuration. In some embodiments, the annular valve body may be biased to assume a radially-expanded configuration; this may be due, at least in part, to the shape memory properties of the annular valve body. As a result, the annular valve body may expand back into the radially-expanded configuration after being radially contracted. For example, FIG. 5E illustrates an exemplary annular valve body 2020 in a radially-expanded configuration. Annular valve body 2020 may be biased to expand to the configuration illustrated in FIG. 5E, due in part to the shape memory properties of the annular valve body. In some embodiments, a constraint (e.g., a radially-constraining delivery device) may exert a radially-contracting force on the annular valve body, causing it to radially contract and preventing the annular valve body from expanding. Upon removal of the constraining force, the annular valve body may be configured to expand back to its pre-contraction expanded configuration (e.g., the configuration illustrated in FIG. 5E).

In some embodiments, the exemplary method of implanting an expandable prosthetic valve may include advancing the ventricular anchors in an atrial direction prior to expanding the annular valve body. As a result of advancing the ventricular anchors in an atrial direction, the ventricular anchors may engage tissue of the native mitral valve. In some embodiments, advancing the ventricular anchors in an atrial direction may occur after the ventricular anchors are released in the atrium and moved into the ventricle and prior to release of the atrial anchors and annular valve body. In some embodiments, the ventricular anchors may engage ventricular tissue of the native mitral valve; for example, the ventricular anchors may grasp the mitral valve tissue and hold it in place during expansion of the remainder of the prosthetic valve. An example of advancing the ventricular anchors in an atrial direction is illustrated in FIGS. 10D and 10E. In FIG. 10D, the released ventricular anchoring legs 2240 (i.e., the exemplary ventricular anchors) are moved into ventricle 9020. In FIG. 10E, the released ventricular anchoring legs 2240 are then moved in an atrial direction (that is, towards atrium 9010) until legs 2240 engage the ventricular-side tissue of mitral valve 9030.

The foregoing description has been presented for purposes of illustration. It is not exhaustive and is not limited to precise forms or embodiments disclosed. Modifications and adaptations of the embodiments will be apparent from consideration of the specification and practice of the disclosed embodiments. For example, while certain components have been described as being coupled to one another, such components may be integrated with one another or distributed in any suitable fashion.

Moreover, while illustrative embodiments have been described herein, the scope includes any and all embodiments having equivalent elements, modifications, omissions, combinations (e.g., of aspects across various embodiments), adaptations and/or alterations based on the present disclosure. The elements in the claims are to be interpreted broadly based on the language employed in the claims and not limited to examples described in the present specification or during the prosecution of the application, which examples are to be construed as nonexclusive. Further, the steps of the disclosed methods can be modified in any manner, including reordering steps and/or inserting or deleting steps.

The features and advantages of the disclosure are apparent from the detailed specification, and thus, it is intended that the appended claims cover all systems and methods falling within the true spirit and scope of the disclosure. As used herein, the indefinite articles "a" and "an" mean "one or more." Similarly, the use of a plural term does not necessarily denote a plurality unless it is unambiguous in the given context. Words such as "and" or "or" mean "and/or" unless specifically directed otherwise. Further, since numerous modifications and variations will readily occur from studying the present disclosure, it is not desired to limit the disclosure to the exact construction and operation illustrated and described, and, accordingly, all suitable modifications and equivalents may be resorted to, falling within the scope of the disclosure.

Other embodiments will be apparent from consideration of the specification and practice of the embodiments disclosed herein. It is intended that the specification and examples be considered as example only, with a true scope and spirit of the disclosed embodiments being indicated by the following claims.

What is claimed is:

1. A method of implanting an expandable prosthetic valve within a native mitral valve between an atrium and a ventricle, the method comprising:
   releasing terminal ends of ventricular anchors of the prosthetic valve from a constrained delivery position of the ventricular anchors by distally advancing a distal capsule portion relative to a remaining portion of a delivery capsule which houses the prosthetic valve in a constrained delivery position, such that by the releasing, the terminal ends of the ventricular anchors move outwardly, while the ventricular anchors are positioned within the atrium;
   after releasing the terminal ends of the ventricular anchors positioned within the atrium, advancing at least a portion of the expandable prosthetic valve containing the ventricular anchors through the native mitral valve into the ventricle;
   releasing terminal ends of atrial anchors of the prosthetic valve relative to a portion of an annular valve body of the prosthetic valve by proximally retracting a proximal capsule portion relative to the delivery capsule, such that by the releasing, the terminal ends of the atrial anchors move outwardly, while the atrial anchors are at least partially positioned within the atrium; and
   after releasing the terminal ends of the ventricular anchors and releasing the terminal ends of the atrial anchors, further distally advancing the distal capsule portion such that the annular valve body expands radially while the ventricular anchors are in the ventricle and the atrial anchors are in the atrium, thereby anchoring native heart valve tissue between the atrial anchors and ventricular anchors.

2. The method of claim 1, wherein the ventricular anchors and the atrial anchors are biased to assume respective expanded configurations.

3. The method of claim 1, wherein further distally advancing the distal capsule portion comprises enabling the annular valve body to expand to a pre-contraction expanded configuration.

4. The method of claim 1, wherein further distally advancing the distal capsule portion comprises enabling the annular valve body to expand within the ventricle.

5. The method of claim 1, further comprising:
   prior to further distally advancing the distal capsule portion, advancing the ventricular anchors in an atrial direction such that the ventricular anchors engage tissue of the native mitral valve.

6. A method of implanting an expandable prosthetic valve within a native mitral valve between a heart atrium and a heart ventricle, the prosthetic valve constrained in a radially-contracted configuration during delivery and including an annular valve body, a plurality of ventricular anchors, and a plurality of atrial anchors, the plurality of atrial anchors and the plurality of ventricular anchors being connected to and extending from the annular valve body, the method comprising:
   releasing the plurality of ventricular anchors from the radially-contracted configuration by distally advancing a distal capsule portion relative to a remaining portion of a delivery capsule which houses the prosthetic valve in the radially-contracted configuration, such that terminal ends of the ventricular anchors deflect radially outward, relative to the annular valve body, while the ventricular anchors are situated within the atrium;
   releasing the plurality of atrial anchors from the radially-contracted configuration while the atrial anchors are situated within the atrium by proximally retracting a proximal capsule portion relative to the delivery capsule;
   moving the released ventricular anchors through the mitral valve and into the ventricle; and
   after moving the released ventricular anchors from the atrium to the ventricle, releasing the annular valve body by further distally advancing the distal capsule portion while the released ventricular anchors are in the ventricle and the released atrial anchors are in the atrium, thereby anchoring the prosthetic valve within the mitral valve, wherein the atrial anchors are released prior to release of the ventricular anchors.

7. A method of implanting an expandable prosthetic valve within a native mitral valve between a heart atrium and a heart ventricle, the prosthetic valve constrained in a radially-contracted configuration during delivery and including an annular valve body, a plurality of ventricular anchors, and a plurality of atrial anchors, the plurality of atrial anchors and the plurality of ventricular anchors being connected to and extending from the annular valve body, the method comprising:

releasing the plurality of ventricular anchors from the radially-contracted configuration by distally advancing a distal capsule portion relative to a remaining portion of a delivery capsule which houses the prosthetic valve in the radially-contracted configuration, such that terminal ends of the ventricular anchors deflect radially outward, relative to the annular valve body, while the ventricular anchors are situated within the atrium;

releasing the plurality of atrial anchors from the radially-contracted configuration while the atrial anchors are situated within the atrium by proximally retracting a proximal capsule portion relative to the delivery capsule;

moving the released ventricular anchors through the mitral valve and into the ventricle; and after moving the released ventricular anchors from the atrium to the ventricle, releasing the annular valve body by further distally advancing the distal capsule portion while the released ventricular anchors are in the ventricle and the released atrial anchors are in the atrium, thereby anchoring the prosthetic valve within the mitral valve, wherein the annular valve body is constrained from expansion during release of the ventricular anchors and atrial anchors and during movement of the ventricular anchors into the ventricle.

8. A method of implanting an expandable prosthetic valve within a native mitral valve between a heart atrium and a heart ventricle, the prosthetic valve constrained in a radially-contracted configuration during delivery and including an annular valve body, a plurality of ventricular anchors, and a plurality of atrial anchors, the plurality of atrial anchors and the plurality of ventricular anchors being connected to and extending from the annular valve body, the method comprising:

releasing the plurality of ventricular anchors from the radially-contracted configuration by distally advancing a distal capsule portion relative to a remaining portion of a delivery capsule which houses the prosthetic valve in the radially-contracted configuration, such that terminal ends of the ventricular anchors deflect radially outward, relative to the annular valve body, while the ventricular anchors are situated within the atrium;

releasing the plurality of atrial anchors from the radially-contracted configuration while the atrial anchors are situated within the atrium by proximally retracting a proximal capsule portion relative to the delivery capsule;

moving the released ventricular anchors through the mitral valve and into the ventricle; and after moving the released ventricular anchors from the atrium to the ventricle, releasing the annular valve body by further distally advancing the distal capsule portion while the released ventricular anchors are in the ventricle and the released atrial anchors are in the atrium, thereby anchoring the prosthetic valve within the mitral valve, wherein the annular valve body radially expands when released.

9. A method of implanting an expandable prosthetic valve within a native mitral valve between a heart atrium and a heart ventricle, the prosthetic valve constrained in a radially-contracted configuration during delivery and including an annular valve body, a plurality of ventricular anchors, and a plurality of atrial anchors, the plurality of atrial anchors and the plurality of ventricular anchors being connected to and extending from the annular valve body, the method comprising:

releasing the plurality of ventricular anchors from the radially-contracted configuration by distally advancing a distal capsule portion relative to a remaining portion of a delivery capsule which houses the prosthetic valve in the radially-contracted configuration, such that terminal ends of the ventricular anchors deflect radially outward, relative to the annular valve body, while the ventricular anchors are situated within the atrium;

releasing the plurality of atrial anchors from the radially-contracted configuration while the atrial anchors are situated within the atrium by proximally retracting a proximal capsule portion relative to the delivery capsule;

moving the released ventricular anchors through the mitral valve and into the ventricle; and after moving the released ventricular anchors from the atrium to the ventricle, releasing the annular valve body by further distally advancing the distal capsule portion while the released ventricular anchors are in the ventricle and the released atrial anchors are in the atrium, thereby anchoring the prosthetic valve within the mitral valve, wherein each ventricular anchor includes a connection point to the annular valve body; and wherein:

during movement of the ventricular anchors into the ventricle, the connection points of the ventricular anchors are arranged in a manner in which the connection points collectively form a first diameter, and the releasing of the annular valve body moves the connection points of the ventricular anchors in a manner in which the connection points collectively form a second diameter after release of the annular valve body, the second diameter being larger than the first diameter.

* * * * *